(12) United States Patent
Chanduszko

(10) Patent No.: US 12,076,042 B2
(45) Date of Patent: Sep. 3, 2024

(54) ABRASIVE ELEMENTS FOR ROTATIONAL ATHERECTOMY SYSTEMS

(71) Applicant: Bard Peripheral Vascular, Franklin Lakes, NJ (US)

(72) Inventor: Andrzej Chanduszko, Chandler, AZ (US)

(73) Assignee: Bard Peripheral Vascular, Franklin Lakes, NJ (US)

( * ) Notice: Subject to any disclaimer, the term of this patent is extended or adjusted under 35 U.S.C. 154(b) by 839 days.

(21) Appl. No.: 16/843,964

(22) Filed: Apr. 9, 2020

(65) Prior Publication Data
US 2020/0237400 A1 Jul. 30, 2020

Related U.S. Application Data

(62) Division of application No. 15/541,341, filed as application No. PCT/US2014/072842 on Dec. 30, 2014, now Pat. No. 10,646,248.

(51) Int. Cl.
A61B 17/3207 (2006.01)
A61B 17/32 (2006.01)

(52) U.S. Cl.
CPC ........... *A61B 17/320725* (2013.01); *A61B 17/320758* (2013.01); *A61B 2017/320004* (2013.01); *A61B 2017/320052* (2013.01); *A61B 2017/320766* (2013.01); *A61B 2217/005* (2013.01); *A61B 2217/007* (2013.01)

(58) Field of Classification Search
CPC .... A61B 17/320725; A61B 17/320758; A61B 2217/005; A61B 2217/007; A61B 2017/320052; A61B 2017/320766; A61B 2017/320004

See application file for complete search history.

(56) References Cited

U.S. PATENT DOCUMENTS

| 5,030,201 A * | 7/1991 | Palestrant ...... A61B 17/320725 600/568 |
| 5,314,438 A | 5/1994 | Shturman |
| 5,376,100 A | 12/1994 | Lefebvre |

(Continued)

FOREIGN PATENT DOCUMENTS

| CN | 102573670 B | 2/2016 |
| JP | 2012526606 A | 11/2012 |
| WO | 2009145973 A2 | 12/2009 |

OTHER PUBLICATIONS

Notice of Allowance dated Jul. 7, 2023, pertaining to Japanese patent Application No. 2021-207232.

(Continued)

*Primary Examiner* — Anh T Dang
(74) *Attorney, Agent, or Firm* — Dinsmore & Shohl LLP

(57) ABSTRACT

A method of ablating a lesion in a vessel includes advancing a guidewire through the vessel; advancing a sheath over the guidewire, the sheath having a proximal end, a distal end, and a lumen extending therethrough; advancing a flexible driveshaft over the guidewire and through the sheath, the driveshaft having a proximal end, a distal end, and an abrasive element attached thereto, the abrasive element having a first diameter; advancing the abrasive element out of the distal end of the sheath; increasing the first diameter of the abrasive element by rotating the driveshaft; and ablating the lesion.

20 Claims, 30 Drawing Sheets

(56) References Cited

U.S. PATENT DOCUMENTS

| | | |
|---|---|---|
| 6,096,054 A * | 8/2000 | Wyzgala .......... A61B 17/320725 |
| | | 606/180 |
| 6,451,037 B1 | 9/2002 | Chandrasekaran et al. |
| 8,177,801 B2 | 5/2012 | Kallok et al. |
| 8,597,313 B2 | 12/2013 | Thatcher et al. |
| 2004/0158270 A1 | 8/2004 | Wyzgala et al. |
| 2009/0105736 A1 | 4/2009 | Prudnikov et al. |
| 2009/0299392 A1 | 12/2009 | Rivers |
| 2009/0306690 A1 | 12/2009 | Rivers |
| 2012/0150207 A1 | 6/2012 | Shturman |
| 2013/0245654 A1 | 9/2013 | Shturman |
| 2014/0081298 A1 | 3/2014 | Cambronne |
| 2014/0277010 A1 | 9/2014 | Weber et al. |
| 2017/0348018 A1 | 12/2017 | Chanduszko |

OTHER PUBLICATIONS

Office Action dated Apr. 1, 2023 pertaining CN application 202010422719.X.

CN Office Action dated Oct. 12, 2023 pertaining to CN application No. 202010422719.X.

\* cited by examiner

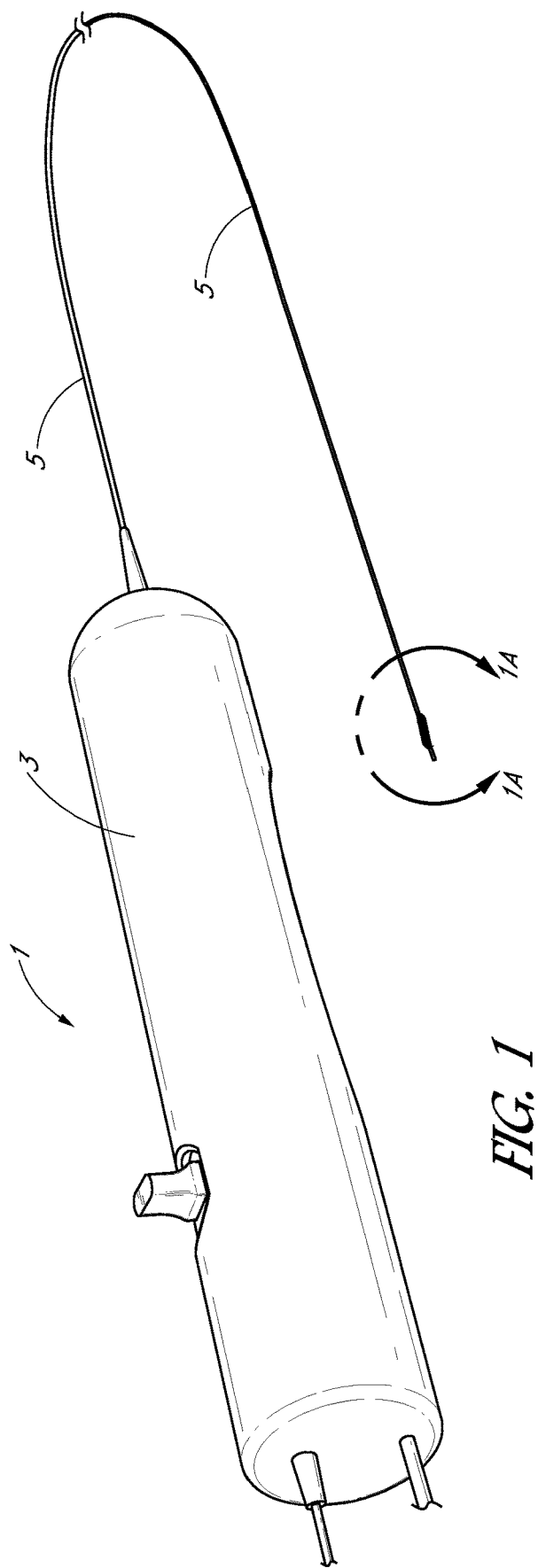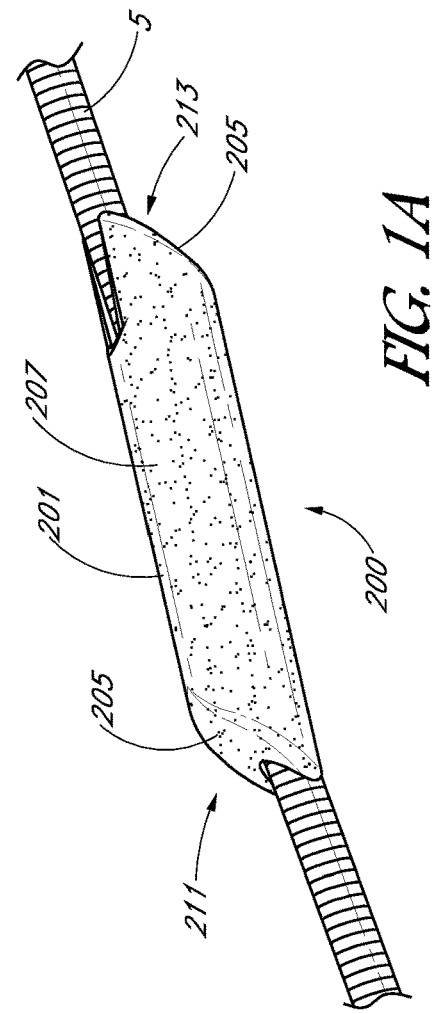
FIG. 1
FIG. 1A

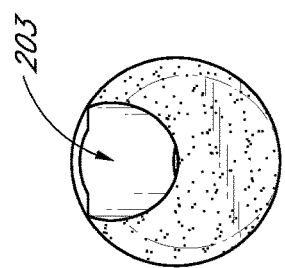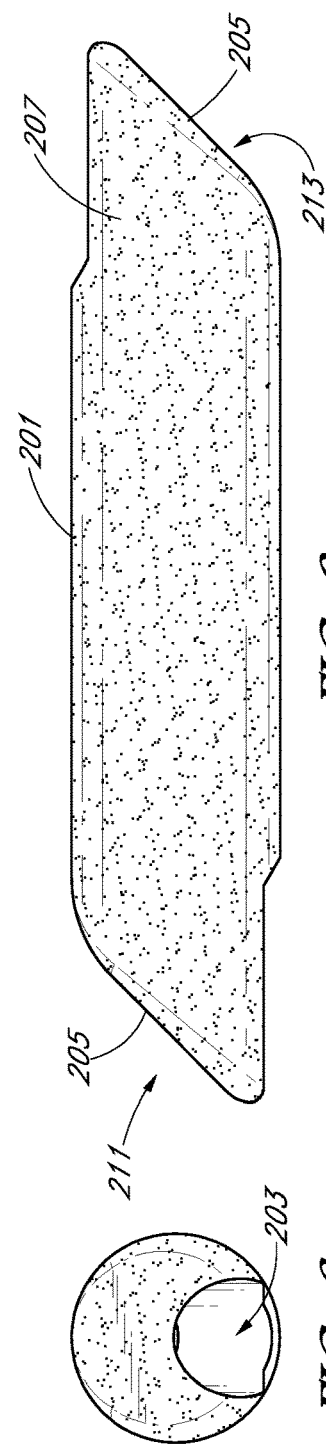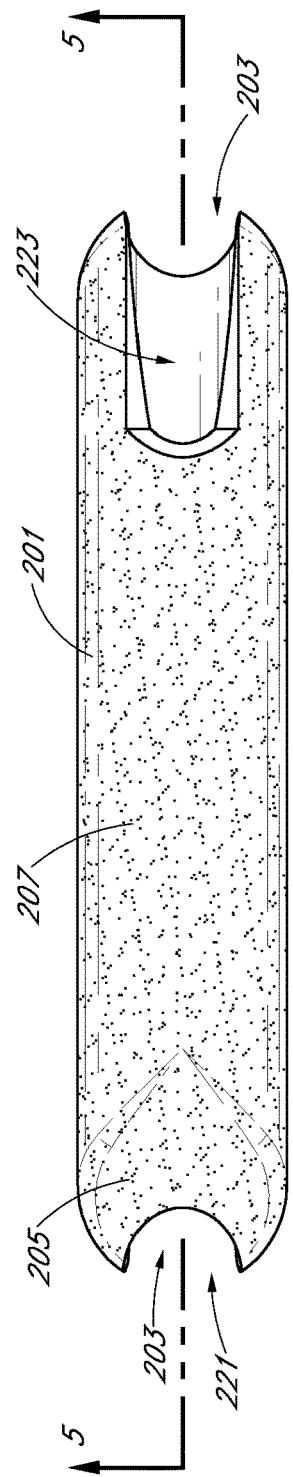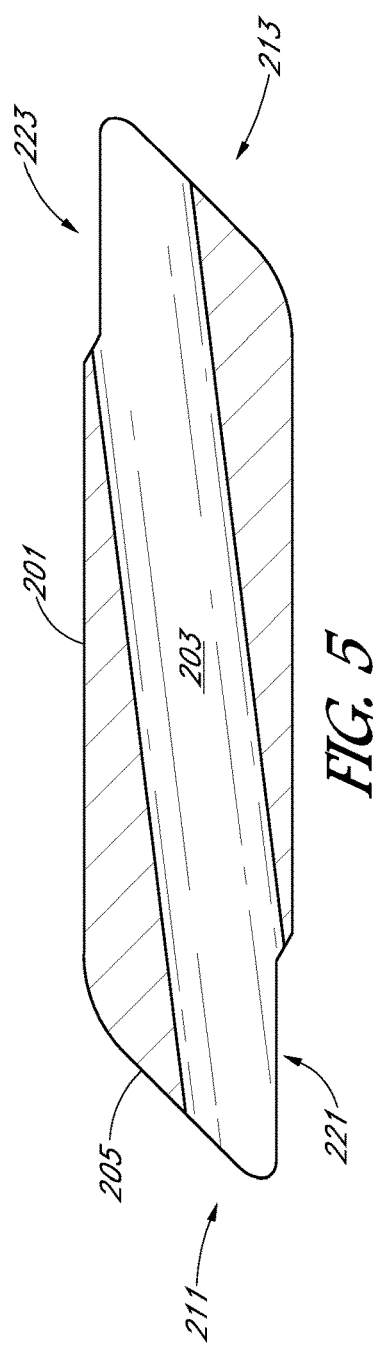

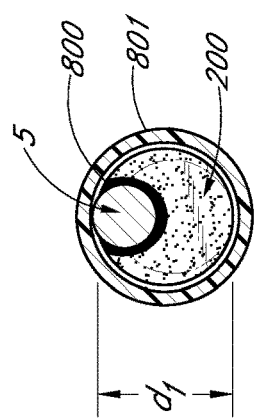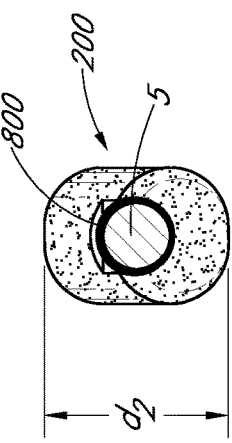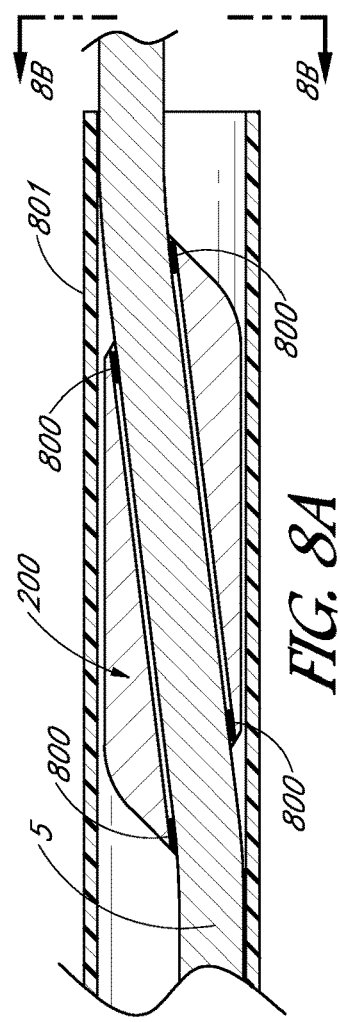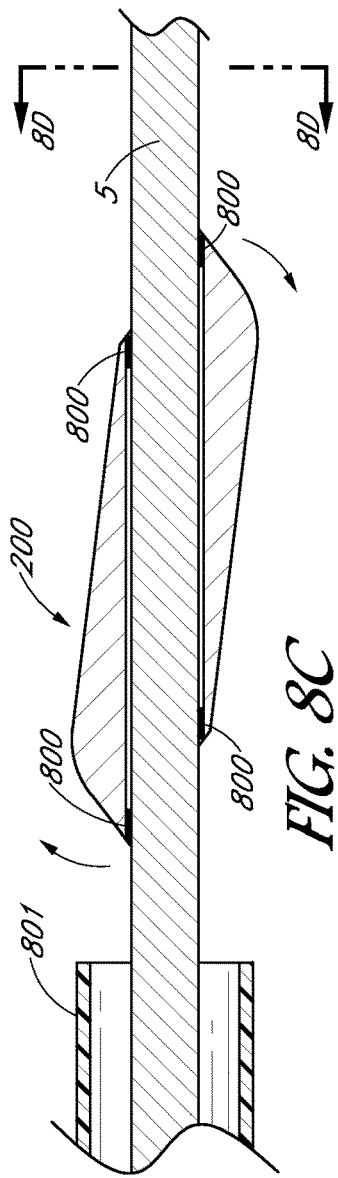

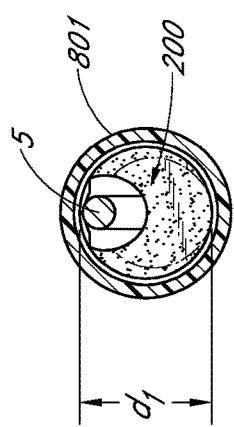
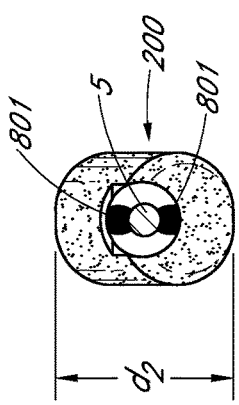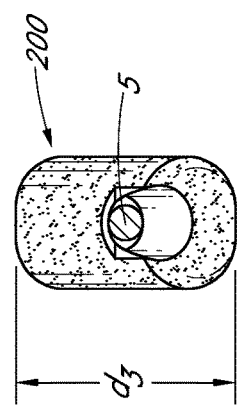
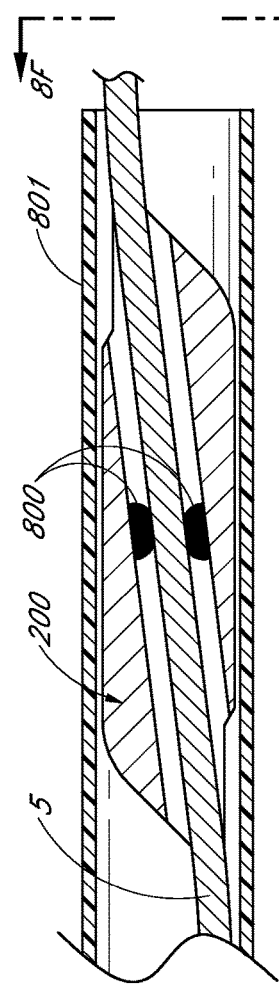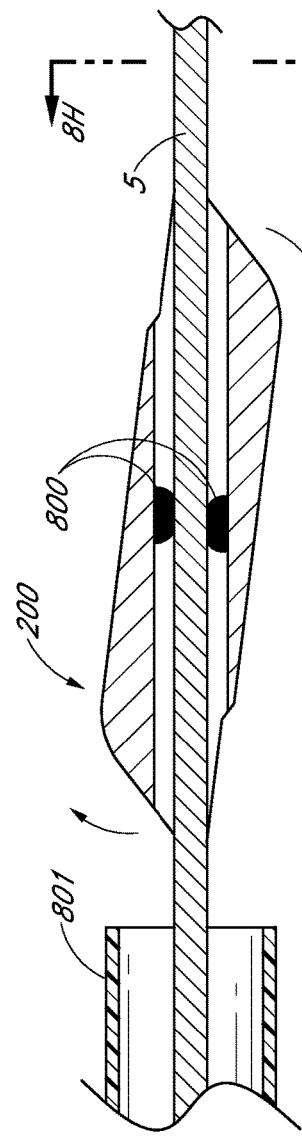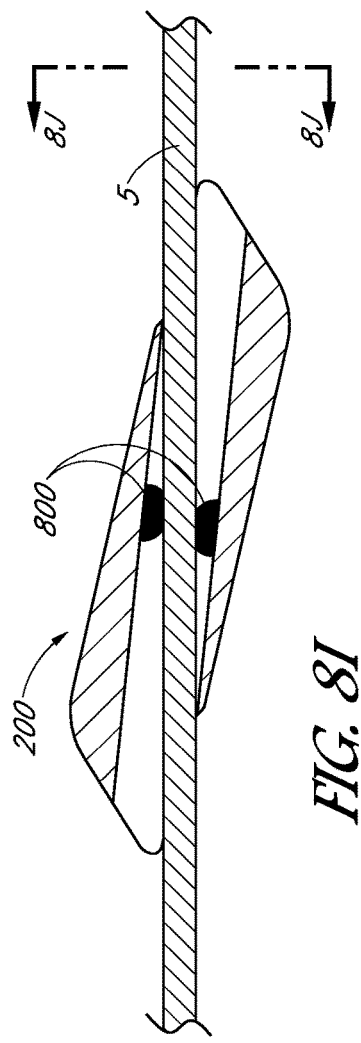

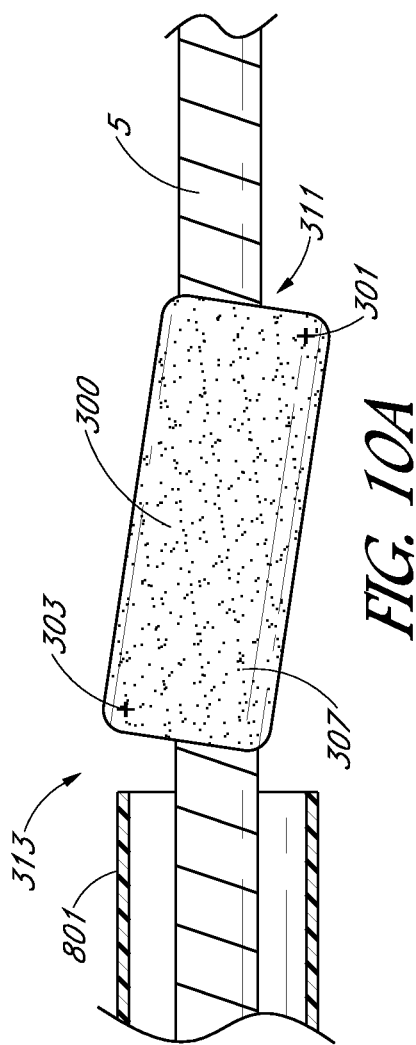
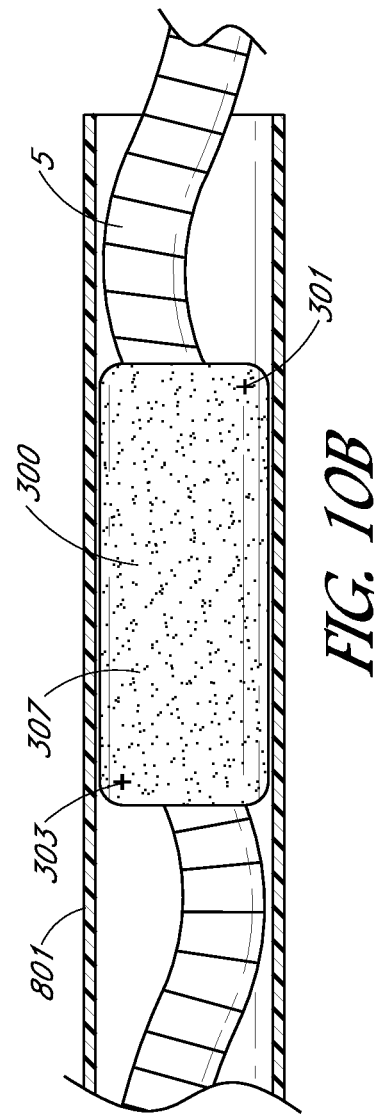

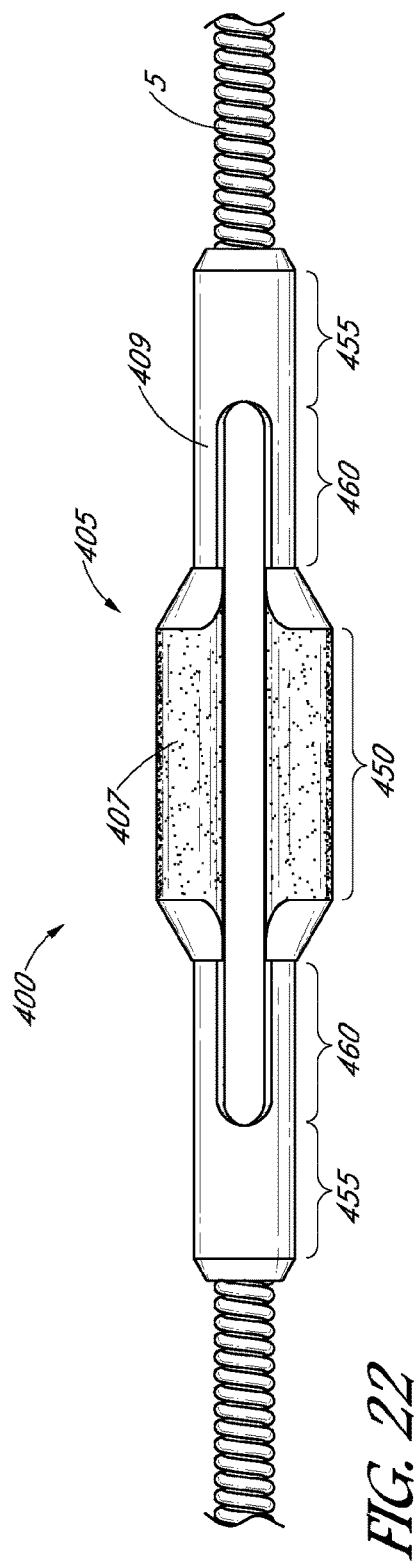
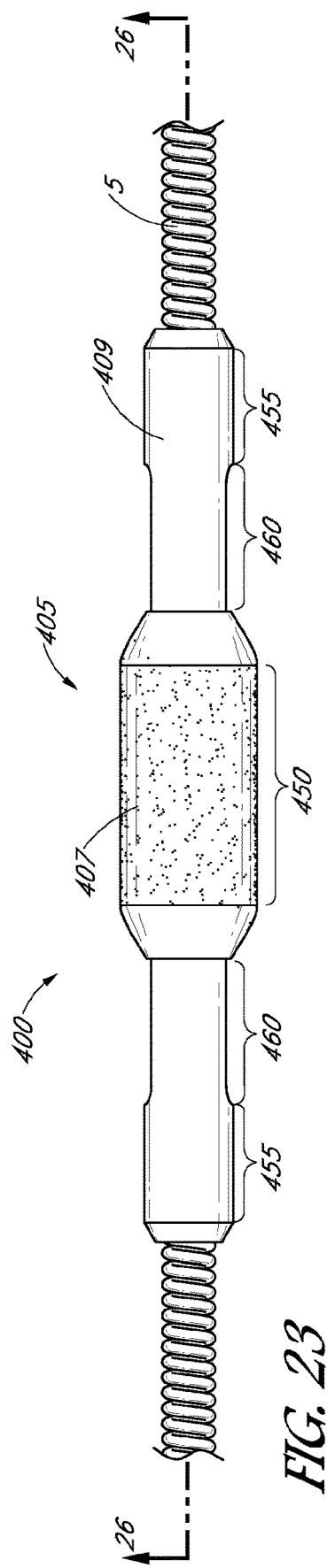
FIG. 22
FIG. 23

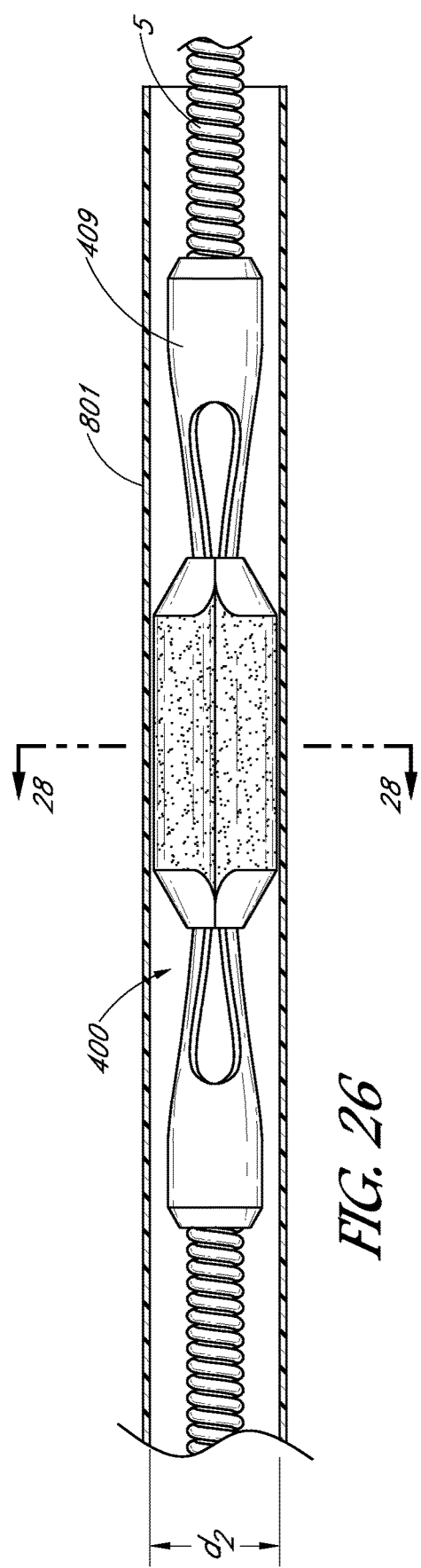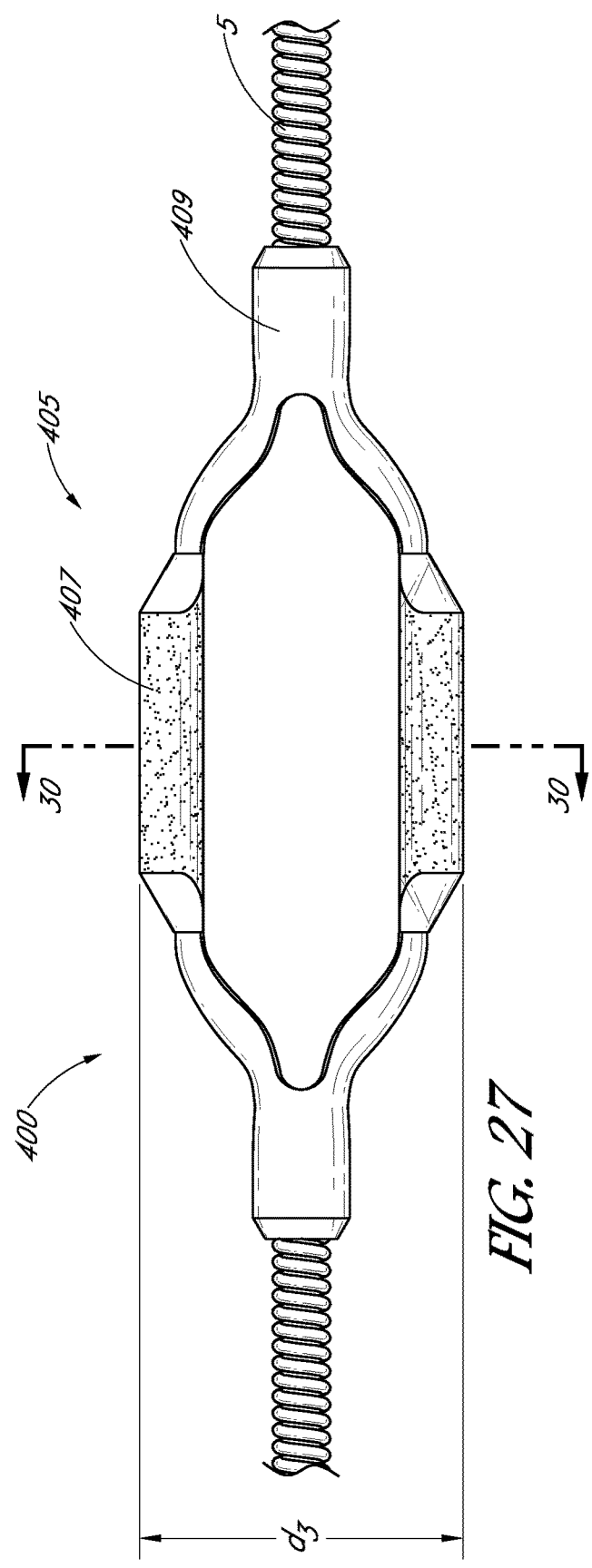
FIG. 26
FIG. 27

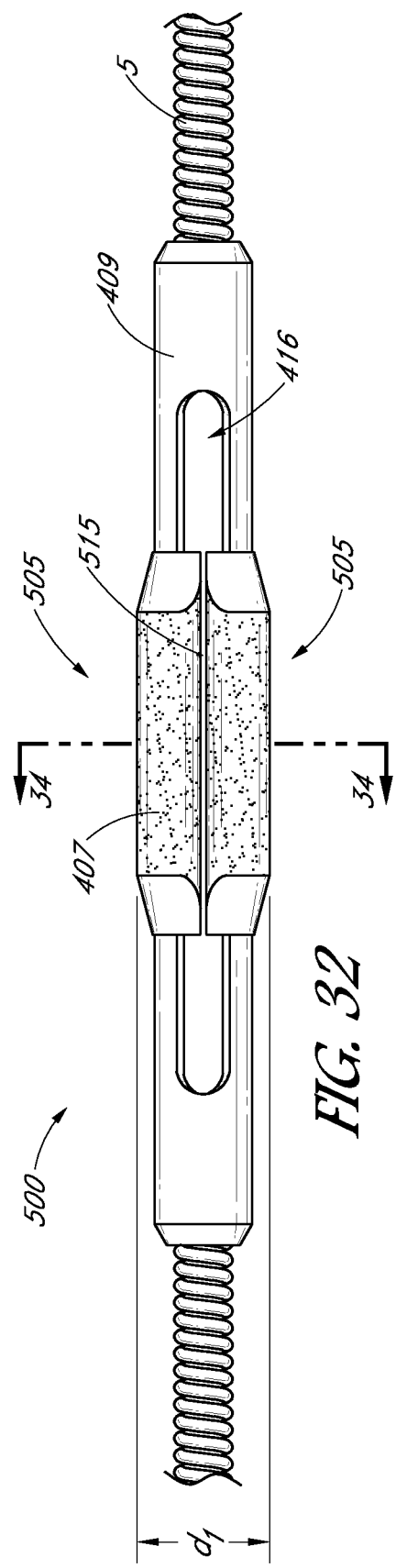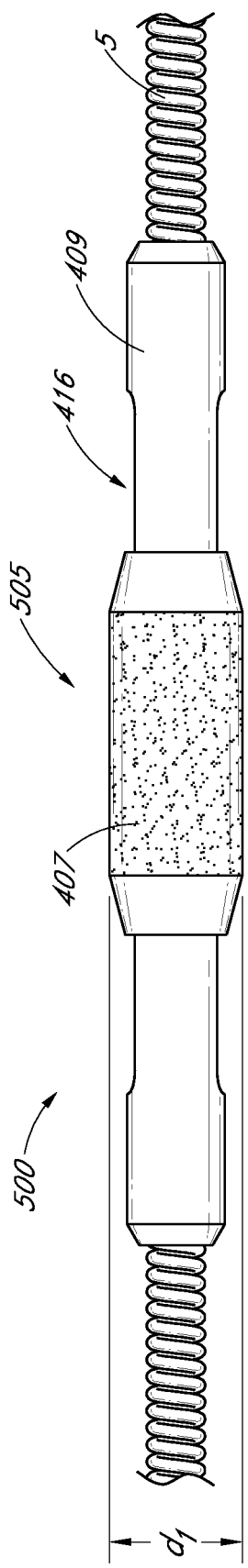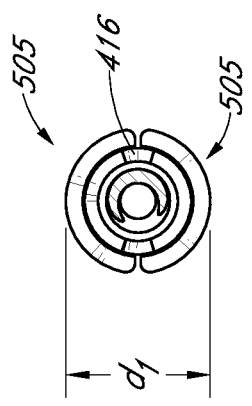

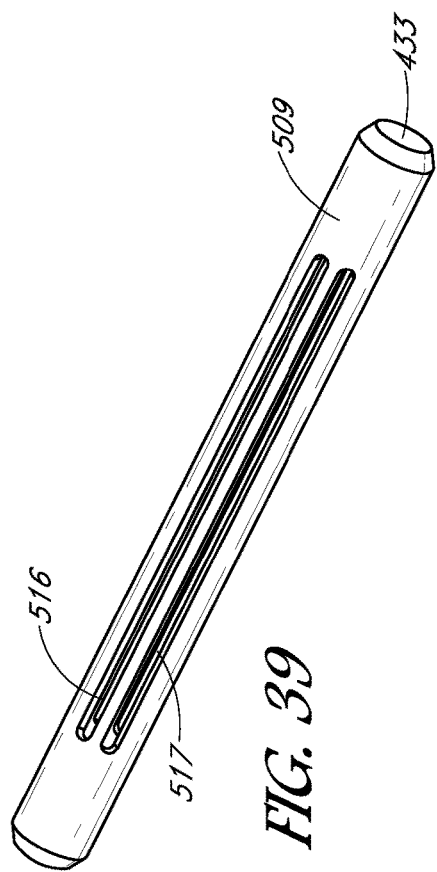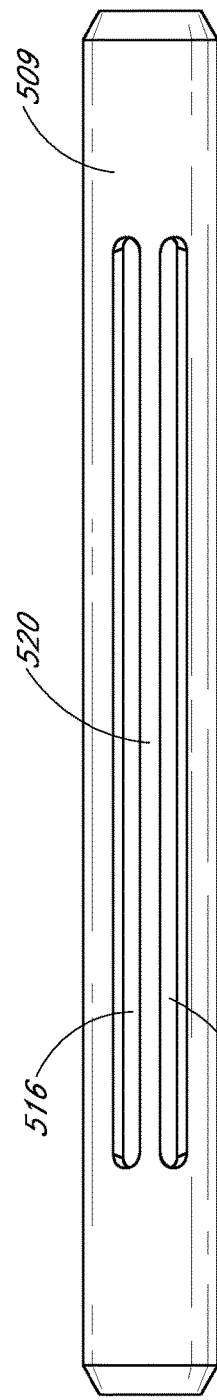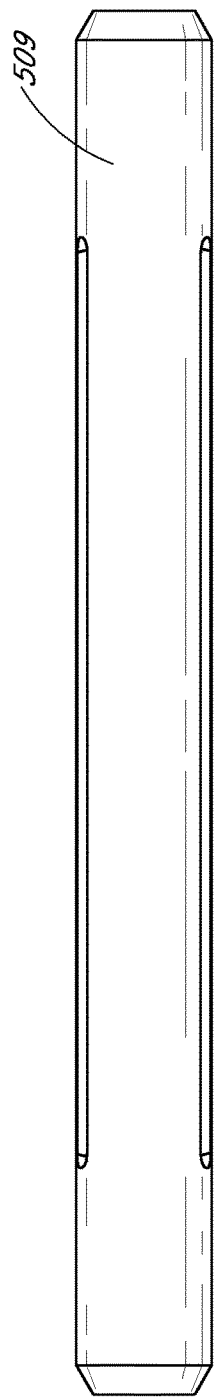
FIG. 42
FIG. 39
FIG. 40
FIG. 41

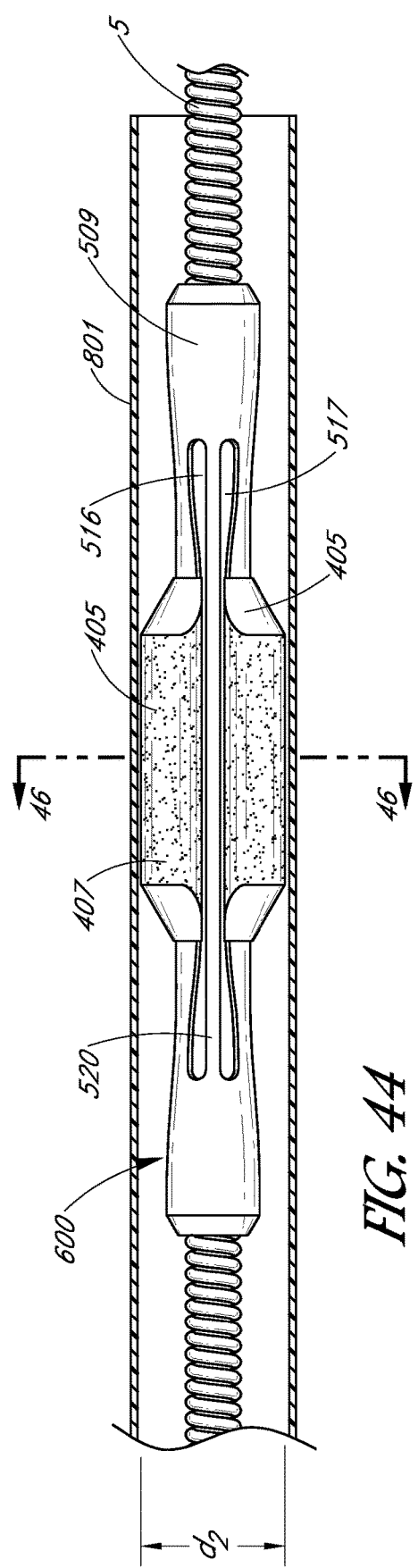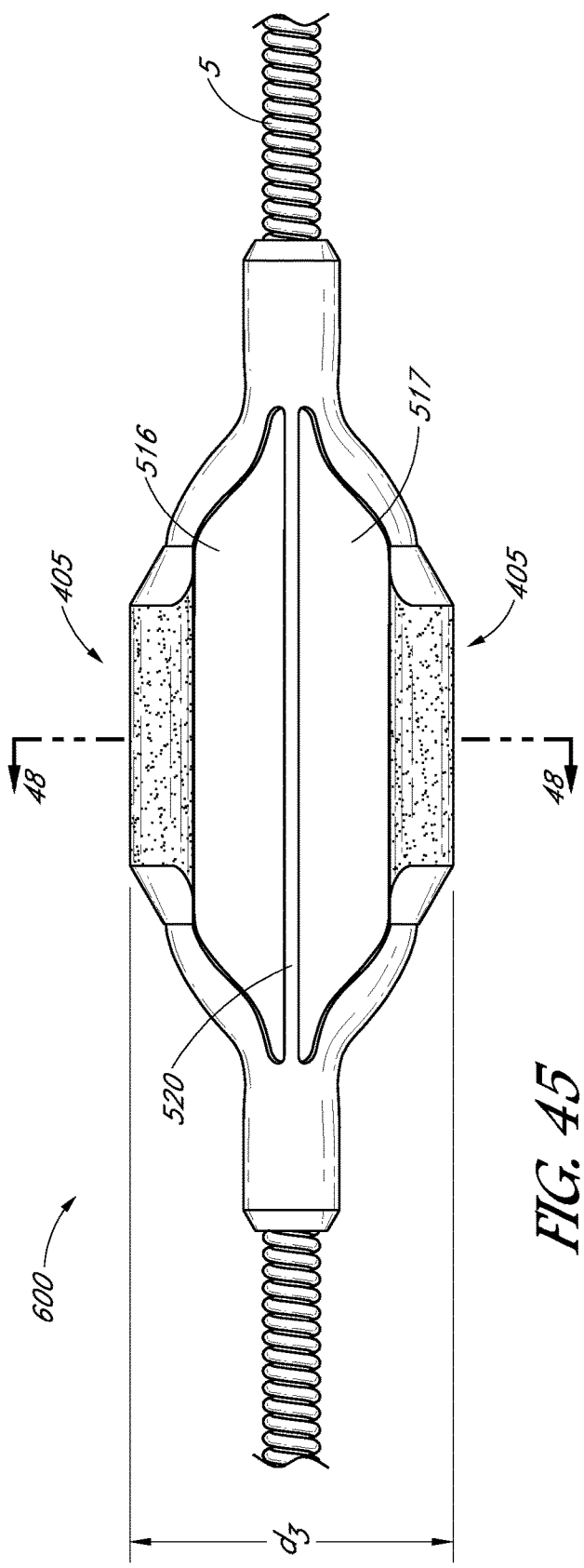

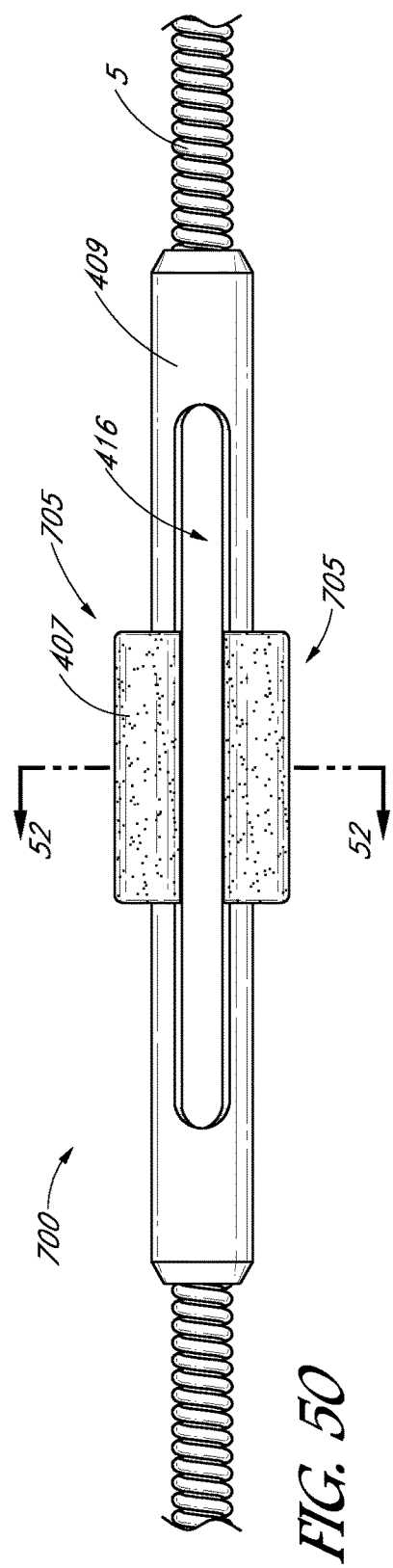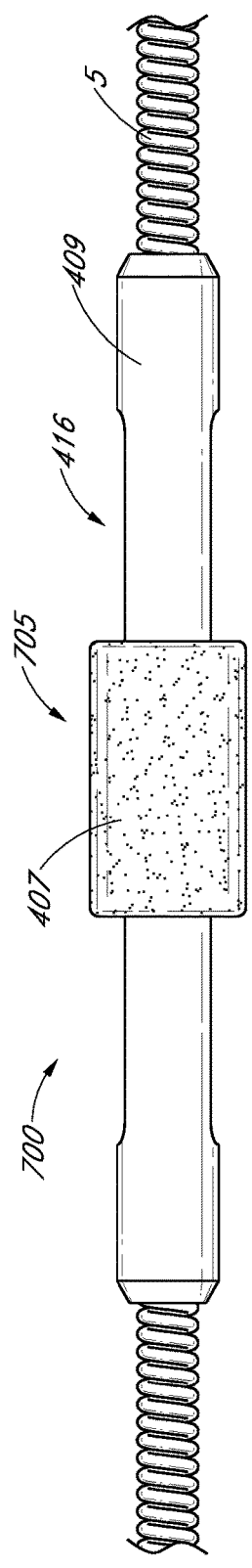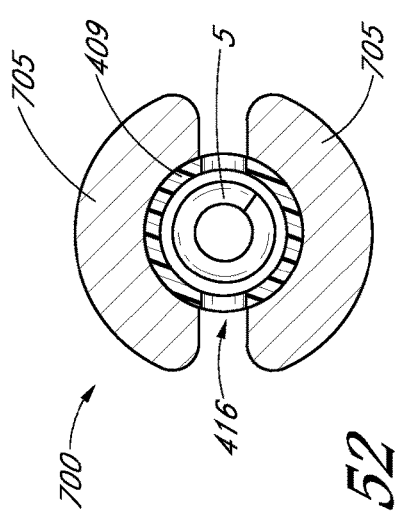
FIG. 50
FIG. 51
FIG. 52

ABRASIVE ELEMENTS FOR ROTATIONAL ATHERECTOMY SYSTEMS

RELATED APPLICATIONS

This application is a divisional of U.S. patent application Ser. No. 15/541,341, filed Jun. 30, 2017, which is a U.S. national stage application under 35 U.S.C. § 371 of International Application No. PCT/US2014/072842, filed Dec. 30, 2014, each of which is incorporated in its entirety herein.

BACKGROUND

Field

The present disclosure is generally directed to atherectomy systems, devices, and methods. More specifically, the present disclosure is directed to novel geometries for abrasive elements used in atherectomy procedures.

Description of the Related Art

Atherosclerosis is a leading cause of coronary heart disease. Atherosclerosis occurs when fat, cholesterol, and/or other substances build up in the walls of blood vessels, forming hard structures called plaques and/or atherosclerotic lesions. Over time, these plaques and/or lesions may increase in size such that the blood vessels are clogged and/or completely blocked.

Rotational atherectomy is a technique used to abrade, for example, calcified arterial lesions. Rotational atherectomy devices and rotational atherectomy procedures may also be referred to as rotational angioplasty devices and/or rotational angioplasty procedures. One type of rotational atherectomy device is known as an orbital atherectomy device.

Rotational atherectomy devices may include an abrasive element attached to a proximal portion of a rotatable flexible driveshaft. The rotatable flexible driveshaft may be delivered over a guidewire and/or through a sheath to a desired location. The abrasive element may be referred to as a burr, crown, and/or bead. The driveshaft may be rotated at high speeds (e.g., between 20,000-160,000 rpm). As the abrasive element rotates, it may be advanced over a stenotic lesion or plaque such that the abrasive element contacts the occluding tissue and/or plaque. In this way, the abrasive element rubs against the lesion surfaces and abrades the lesion into very small particles. These small particles may be removed from the site by blood flow.

SUMMARY

The devices, systems, and methods of the present disclosure have several features, no single one of which is solely responsible for its desirable attributes. Without limiting the scope of this invention as expressed by the claims which follow, its more prominent features will now be discussed briefly. After considering this discussion, and particularly after reading the section titled "Detailed Description of Certain Embodiments," one will understand how the features of this disclosure provide several advantages over other rotational atherectomy systems.

The present disclosure is directed to novel bead geometries that can provide improved sanding efficiencies in atherectomy procedures. One embodiment is a high-speed rotational atherectomy device for opening a stenosis in an artery having lumen extending therethrough. The device may comprise a flexible, elongated, rotatable driveshaft. The device may also include guidewire having a maximum diameter less than the diameter of the lumen. In such embodiments the driveshaft may be advanceable over the guidewire. An abrasive element may be disposed on the driveshaft. The abrasive element may have a first center of mass offset from a center of mass of the driveshaft in a first radial direction. The abrasive element may have a second center of mass offset from a center of mass of the driveshaft in a second radial direction. The second center of mass may be positioned proximal of the first center of mass. The second radial direction may be predominantly opposite to the first radial direction. In some aspects, the abrasive element is eccentric in shape.

The abrasive element may have a proximal end and a distal end. The abrasive element may have an overall center of mass that is located between the proximal end and the distal end. In some embodiments, the overall center of mass may be located at the midway point between the proximal end and the distal end. The distal end may have a center of mass that is offset from a center of mass of the driveshaft in a first radial direction. The proximal end may have a center of mass that is offset from the center of mass of the driveshaft in a second radial direction. The second radial direction may be in the opposite direction of the first radial direction. In some aspects, the abrasive element includes a waist disposed between the proximal end and the distal end of the abrasive element. In some aspects, at least a portion of the exterior facing surfaces are roughened, that is: rough compared to exterior surfaces of the driveshaft. In some aspects, the centers of mass include a heavier material than the remainder of the abrasive element. In other words, the center of mass of the abrasive elements may include a material that has a higher density than the density of the material of the remainder of the abrasive element. In some aspects, the abrasive element is disposed on the driveshaft in a manner so as to allow the abrasive element to move in a radial direction with respect to the driveshaft. It is not inconceivable that for one embodiment the abrasive element comprises a distal portion, a middle portion, and a proximal portion. In such an embodiment, each of these portions may have a center of mass offset in a radial direction which may, for the distal and proximal portions, be more or less the same direction. For the middle portion, the offset may be in a direction that is predominantly opposite the direction of offset for the distal and proximal portions. The center of mass of the distal and proximal portions taken in combination may be proximal or distal, from a longitudinal perspective of the driveshaft, from the center of mass of the middle portion. However, it is also not inconceivable that the center of mass of the distal portion and the proximal portion, taken in combination, coincides with the center of mass of the middle portion: with respect to a longitudinal position along the driveshaft. The centers of mass may be in balance with respect to the driveshaft or slightly out of balance.

Another embodiment is a high-speed rotational atherectomy device for opening a stenosis in an artery having a lumen extending therethrough. The device may include a flexible, elongated, rotatable driveshaft sized and shaped for insertion into the lumen. The device may also include a body. The body may have a radially expandable structure at a location between a distal end and a proximal end thereof. At least two abrasive elements may be disposed on an outer surface of the body and be distributed around the radially expandable structure so that when rotating the driveshaft, the at least two abrasive elements pull away from each other and increase a dimension of the radially expandable structure, there between, in a radial direction. The body may have a slot extending through a side of the body at a location between a distal end and a proximal end of the body. The proximal and distal ends may be coupled to the flexible, elongated, rotatable driveshaft. The body and the driveshaft may be advanceable over a guidewire. The body may comprise an elongated tube. The abrasive elements may be disposed on opposite sides of the slot. When the driveshaft is rotated, the at least two abrasive elements may pull away from each other and increase a width of the slot therebetween. In some aspects, the abrasive elements and the body are formed from different materials, that is: the abrasive elements may be formed from a material that is different from a material of which the body is formed. In some aspects, the at least two abrasive elements are disposed at different longitudinal locations along the body. In some embodiments, a bar extends from a proximal end of the slot to a distal end of the slot. The abrasive elements may include an exterior surface which is rough compared to exterior surfaces of the driveshaft. It is not inconceivable that an embodiment comprises three abrasive elements, or more. These may be equally distributed around the radially expandable structure. The centers of mass may be in balance with respect to the driveshaft, or only slightly balance each other out.

Another embodiment comprises a method of ablating a lesion in a vessel. The method may include advancing a guidewire through the vessel. A sheath may be advanced over the guidewire. The sheath may have a proximal end, a distal end, and lumen extending therethrough. The sheath may include an introducer sheath. In aspects, the sheath comprises a catheter having a lumen extending therethrough. The method may also include advancing a flexible driveshaft over the guidewire and through the sheath. The driveshaft may have a proximal end, a distal end, and an abrasive element attached thereto. The abrasive element may have a first diameter. The method may also include advancing the abrasive element out of the distal end of the sheath and increasing the first diameter of the abrasive element by rotating the driveshaft. The method may also include ablating the lesion. In some aspects, the abrasive element is constrained to a second effective that is less than the first diameter when the abrasive element is advanced through the sheath. The diameter may be an effective diameter.

BRIEF DESCRIPTION OF THE DRAWINGS

These and other features, aspects, and advantages of the invention disclosed herein are described below with reference to the drawings of certain embodiments, which are intended to illustrate and not to limit the invention. Additionally, from figure to figure, the same reference numerals have been used to designate the same components of an illustrated embodiment. The following is a brief description of each of the drawings.

FIG. 1 is a schematic perspective view of an atherectomy system that may be used in connection with the abrasive elements disclosed herein. The atherectomy system may include a drive system coupled to a driveshaft. An abrasive element may be coupled to a distal portion of the driveshaft.

FIG. 1A is an enlarged perspective view of the abrasive element that is coupled to the distal portion of the driveshaft shown in FIG. 1.

FIG. 3 is a side view of the abrasive element of FIG. 2.

FIG. 4 is a top view of the abrasive element of FIG. 2.

FIG. 5 is a cross-sectional view of the abrasive element of FIG. 4 along the line 5-5.

FIG. 6 is a front view of the abrasive element of FIG. 3.

FIG. 7 is a rear view of the abrasive element of FIG. 3.

FIG. 8A is a schematic cross-sectional view of the abrasive element of FIG. 2 coupled to a driveshaft and biased against an inner wall of a sheath.

FIG. 8B is a cross-sectional view taken about the line 8B-8B in FIG. 8A.

FIG. 8C is the same as FIG. 8A except that the abrasive element has been removed from the sheath and returned to an unbiased position.

FIG. 8D is a cross-sectional view taken about the line 8D-8D in FIG. 8C.

FIG. 8E is the same as FIG. 8A except that the abrasive element is coupled to the driveshaft in alternative manner. As shown, the abrasive element is biased against an inner wall of a sheath.

FIG. 8F is a cross-sectional view taken about the line 8F-8F in FIG. 8E.

FIG. 8G the same as FIG. 8E except that the abrasive element has been removed from the sheath and returned to an unbiased position.

FIG. 8H is a cross-sectional view taken about the line 8H-8H in FIG. 8G.

FIG. 8I is the same as FIG. 8G when the abrasive element is rotated at high speeds. As shown, at least a portion of the abrasive element may move relative to the driveshaft.

FIG. 8J is a cross-sectional view taken about the line 8J-8J in FIG. 8I.

FIG. 10A is a schematic side-view of an abrasive element according to another embodiment. The abrasive element is similar to the abrasive element of FIG. 2 but may not include a diagonal internal lumen extending therethrough.

FIG. 10B is the same as FIG. 10A except that the abrasive element is shown as biased against an inner wall of a sheath.

FIG. 22 is a side view of the abrasive element of FIG. 11.

FIG. 23 is a top view of the abrasive element of FIG. 11.

FIG. 26 is a side-view of the abrasive element of FIG. 11 positioned within a sheath and in a constrained state.

FIG. 27 is a side-view of the abrasive element of FIG. 11 when the abrasive element is rotated at high speeds. As shown, the abrasive protrusions open the slot as the abrasive element is rotated at high speeds.

FIG. 32 is a side view of the abrasive element of FIG. 31.

FIG. 33 is a top view of the abrasive element of FIG. 31.

FIG. 34 is a cross-sectional view of the abrasive element of FIG. 32 taken about the line 34-34.

FIG. 39 is a perspective view of the double-slotted tube of FIG. 38.

FIG. 40 is a side view of the double-slotted tube of FIG. 38.

FIG. 41 is a top view of the double-slotted tube of FIG. 38.

FIG. 42 is a front view of the double-slotted tube of FIG. 40.

FIG. 44 is a side view of the abrasive element of FIG. 37 positioned within a sheath in a constrained state.

FIG. 45 is a side view of the abrasive element of FIG. 37 when the abrasive element is rotated at high speeds.

FIG. 50 is a side view the abrasive element of FIG. 49.

FIG. 51 is a top view of the abrasive element of FIG. 50.

FIG. 52 is a cross-sectional view of the abrasive element of FIG. 50 taken about the line 52-52.

DETAILED DESCRIPTION OF CERTAIN EMBODIMENTS

Figure 2:
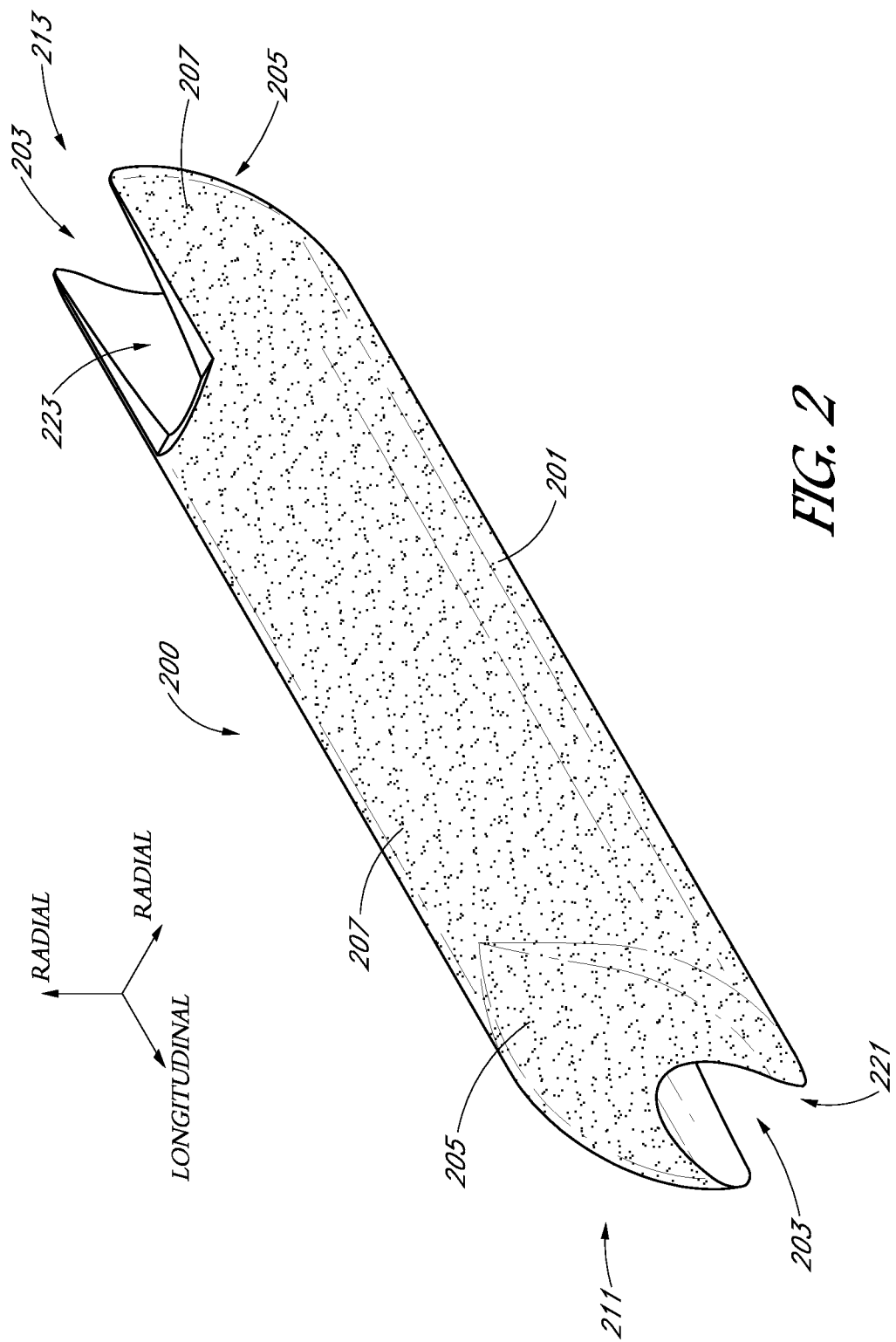
FIG. 2 is an enlarged perspective view of the abrasive element of FIGS. 1 and 1A with the driveshaft removed.

The following description and examples illustrate preferred embodiments of the present rotational atherectomy devices disclosed in the context of use in atherectomy procedures. More specifically, the embodiments relate to rotational atherectomy devices and related techniques that are used to ablate, for example, calcified lesions in blood vessels.

The following description and the accompanying figures, which describe and show the preferred embodiments, are made to demonstrate several possible configurations that an atherectomy device and/or system can take to include the various disclosed aspects and features. Those of skill in the art will recognize that the disclosed aspects and features are not limited to any particular atherectomy system or device, which may include one or more of the inventive aspects and features described herein. Furthermore, the disclosed embodiments can be used in a variety of medical procedures and in connection with a variety of commercially available devices.

Particular implementations of the subject matter described herein can be implemented to realize one or more of the following potential advantages. The atherectomy devices described herein are especially adapted to more efficiently ablate calcified lesions in blood vessels. In some embodiments, the devices include an abrasive element configured such that at least a portion of the abrasive element moves away from the central axis of the driveshaft. In some embodiments the devices include a distal abrasive element configured to expand when the abrasive element is rotated at high speeds. In this way, the abrasive elements disclosed herein may expand further out from the driveshaft and against the lesion. In other words, the abrasive elements disclosed herein have a greater sanding range and/or sweep area than other abrasive elements.

In some embodiments, the abrasive elements may allow for effectively larger abrasive elements to fit through a standard lumen when delivered to the place of interest. For example, the abrasive element may be configured such that it is constricted radially when it is placed within a lumen and then expands radially when it exits the lumen. The abrasive element may be further configured such that it further expands radially when it is rotated. In this way the abrasive elements disclosed herein may open stenotic lesions to a diameter that is substantially larger than the maximum diameter of the abrasive element and/or the sheath that the abrasive element is delivered through. Thus, the abrasive elements disclosed herein may have improved sanding ranges, increased sweep areas, and may reduce treatment times, and/or more effectively prevent re-stenosis.

Various aspects will now be described with reference to specific forms or embodiments selected for purposes of illustration. It will be appreciated that the spirit and scope of the atherectomy systems disclosed herein are not limited to the selected forms. Moreover, it is to be noted that the figures provided herein are not drawn to any particular proportion or scale, and that many variations can be made to the illustrated embodiments. Brief introductions to some of the features, which are common to the described embodiments of the atherectomy systems, are now described.

To assist in the description of these components of the atherectomy systems, the following coordinate terms are used. A "longitudinal axis" is generally parallel to the elongated sides of the abrasive elements disclosed herein. See, e.g., FIG. 2. A "radial axis" is normal to the longitudinal axis and extends in a radial direction.

In addition, as used herein, "the longitudinal direction" refers to a direction substantially parallel to the longitudinal axis and "the radial direction" refers to a direction substantially parallel to a radial axis. The term "axial" may be used herein and is synonymous with the term "longitudinal" as used herein.

Also, the terms "proximal" and "distal," which are used to describe the present atherectomy systems, are used consistently with the description of the exemplary applications (i.e., the particular illustrative examples). Thus, proximal and distal are used in reference to the handle of the atherectomy system.

The terms "upper," "lower," "top," "bottom," "underside," "upperside" and the like, which also are used to describe the present atherectomy system, are used in reference to the illustrated orientation of the embodiment. For example, the term "upperside" may be used to describe the portion of the abrasive element that is located above a longitudinal and/or radial axis that passes through the center of the abrasive element. The term "underside" may be used to describe the portion of the abrasive element that is located below longitudinal and/or radial axis that passes through the center of the abrasive element.

FIG. 1 illustrates a rotational atherectomy system 1 according to one embodiment. The system 1 includes a drive system 3 configured to rotate a flexible driveshaft 5 at high speeds (e.g., 20,000-160,000 rpm). The drive system 3 may include an electric motor. The drive system 3 may include portions of, or be designed substantially similar to, the Boston Scientific Rotablator, the Cardiovascular Systems Inc. ("CSI") Stealth, the CSI Diamondback360, and/or other similar devices. The driveshaft 5 may be advanceable over a guidewire (not shown) or through a sheath. The driveshaft 5 may include a proximal end that is coupled to the drive system 3 and a distal end that is inserted into a patient. The driveshaft 5 may extend through a lumen of, for instance, an artery. In some embodiments, the rotational atherectomy system 1 includes a sheath. In some embodiments, a catheter having a lumen extending therethrough is coupled to a proximal end of the driveshaft. In such an embodiment, the driveshaft 5 may extend through the lumen of the catheter.

As shown in FIG. 1A, an abrasive element 200 may be coupled to a distal portion of the driveshaft 5. In some embodiments that abrasive element 200 is coupled to a location that is proximal to the distal end of the driveshaft 5. For example, the abrasive element 200 may be coupled to the driveshaft 5 at a location that is about 20 mm proximal to the distal end of the driveshaft 5. In some embodiments, the abrasive element 200 is located about 10 mm proximal to the distal end of the driveshaft 5. The driveshaft 5 may comprise a coiled wire. In other embodiments, the driveshaft 5 comprises a tube.

The abrasive element 200 may include a proximal end 213 and a distal end 211. The abrasive element may be between about 1 and 25 mm in length. In other embodiments, the abrasive element is between about 1 and 15 mm in length. In some embodiments, the abrasive element is about 6 mm in length. The abrasive elements disclosed herein may be made of any suitable material or combination thereof. For example, the abrasive elements or portions thereof may be made of surgical stainless steel, titanium, tungsten, nitinol, and the like. In some embodiments, the abrasive element is solid as opposed to hollow. In some embodiments, the abrasive element includes a raised waist disposed between the proximal and distal ends. In some embodiments, the abrasive element has an eccentric shape.

Turning to FIG. 2, an enlarged view of an abrasive element 200 according to the embodiment of FIGS. 1 and 1A is depicted. As illustrated, the abrasive element 200 includes a generally cylindrical bead 201 having sloped ends 205 and a lumen 203 extending therethrough. The abrasive element 200 may be attached to a flexible driveshaft 5 that is rotated by an electric motor at high speeds. In general, the abrasive element 200 is coupled to the driveshaft 5 such that the abrasive element 200 and the driveshaft 5 rotate in unison about a longitudinal axis that passes through the center of the driveshaft 5. That is to say, the abrasive element 200 may be coupled to the driveshaft 5 such that the abrasive element 200 is constrained from moving with respect to the driveshaft 5. In other embodiments, the abrasive element 200 is configured such that the abrasive element 200 is constrained from moving in the longitudinal direction but is not constrained from moving in a transverse and/or lateral longitudinal direction with respect to the driveshaft 5. In some embodiments, the abrasive element 200 moves in concert with at least a portion of the driveshaft 5 that is located within the abrasive element 200.

In some embodiments, at least a portion of the driveshaft 5 positioned within abrasive element 200 is welded to at least a portion of the interior surface of the lumen 203. In certain embodiments, the abrasive element 200 is welded to the entire interior surface of the lumen 203. In other embodiments, the abrasive element 200 is crimped, such that at least a portion of the lumen 203 engages with at least a portion of the driveshaft 5 that is positioned within the lumen 203. In some embodiments, the proximal portion of the lumen is welded to the proximal portion of the driveshaft and the distal portion of the lumen is welded to the distal portion of the driveshaft. For example, in some embodiments, a laser is used to melt at least a portion of the abrasive element 200 to at least a portion of the driveshaft 5.

The abrasive element 200 may include a roughened exterior surface 207. The roughened exterior surface 207 may increase the sanding ability of the abrasive element 200. In some embodiments, the roughened exterior surface 207 includes diamond particles deposited on one or more of the exterior surfaces of the abrasive element 200. A diameter of these particles may be about 20 μm. While the abrasive element 200 is shown as having an entire exterior surface that is roughened, in some embodiments, less than the entire exterior surface is roughened. The roughened exterior surface 207 may be analogous to sandpaper and may increase the ability of the abrasive element 200 to ablate lesions.

The geometry of an example of the abrasive element 200 is further illustrated in FIGS. 3-7. As best shown in FIG. 5, the lumen 203 extending through the abrasive element 200 extends diagonally through the generally cylindrical bead 201. In other words, as shown in FIG. 5, the lumen 203 extends from the bottom-left corner of the distal end 211 of the cylindrical bead 201 to the top-right corner of the proximal end 213 of the cylindrical bead 201. In this way, as shown for example in FIG. 1A, when the abrasive element 200 is attached to a flexible driveshaft 5 that is positioned within the lumen 203, the sloped ends 205 of the abrasive element 200 extend further radially away from the flexible driveshaft 5 than the other exterior surfaces of the abrasive element 200. In this way, the distal 211 and proximal 213 ends may have local centers of mass that are diagonally opposite from one another and at a distance away from the center of the longitudinal axis of the driveshaft 5. For example, as shown in FIG. 1A, the local center of mass of the distal end 211 of the abrasive element 200 is located on the upperside of the driveshaft 5 while the local center of mass of the proximal end 213 of the abrasive element 200 is located on the underside of the driveshaft 5.

In some embodiments, the sloped ends 205 are shaped so as to improve the trackability of the abrasive element 200 through the vasculature. For example, one or more angled surfaces may increase the ability of the abrasive element 200 to be inserted through tortuous paths and/or tight passageways. The sloped ends 205 may also help facilitate the passage of the abrasive element 200 through calcified material in the vessel.

While a generally cylindrical bead 201 is shown, other shapes are contemplated. For example, in some embodiments, the abrasive element 200 may include a waist that is larger or smaller in diameter than the reminder of the generally cylindrical bead 201.

As shown in FIG. 5, the angle of the lumen 203 can create two offset local centers of mass located near the distal and proximal ends of the abrasive element 200. That is to say, the diagonal lumen 203 causes there to be more mass below a longitudinal axis extending through the center of the abrasive element 200 at the proximal end 213 than at the distal end 211. Similarly, the diagonal lumen 203 causes there to be more mass above a longitudinal axis extending through the center of the abrasive element 200 at the distal end 211 than at the proximal end 213.

In other embodiments, the distal and/or proximal ends may be made of a heavier material than the material of the remainder of the abrasive element 200. For example, in some embodiments, the sloped ends 205 and/or at least a portion of the volume disposed under the sloped ends 205 are made of a heavier material than the material of the remainder of the abrasive element 200. For example, in some embodiments, at least a portion of the distal 211 and proximal 213 ends of the generally cylindrical bead 201 are made of tungsten while the remainder of the generally cylindrical bead 201 is made of steel. In this way, the heavier material of the distal 211 and proximal 213 ends may further distribute two masses that are located off-center at opposite ends and opposite sides of the abrasive element 200. In some embodiments, at least a portion of the abrasive element 200 is hollow. For example, in some embodiments at least a portion of the distal end and at least a portion of the proximal end include at least one hollow portion.

During the operation, the distribution of mass in the abrasive element 200 may change the sanding angle of the abrasive element 200 with respect to a longitudinal axis extending through a lumen of a blood vessel. For example, at lower speeds, the sides of the generally cylindrical bead 201 may contact and ablate material that is deposited on the walls of the vessel lumen. At higher speeds, the offset local centers of mass may cause the abrasive element 200 to wobble with respect to a longitudinal axis extending through the vessel. In this way, the sloped ends 205 of the abrasive element 200 may also contact and ablate material that is deposited on the walls of the vessel lumen. In some embodiments, this variable sanding angle of the abrasive element 200 may increase the effectiveness of the atherectomy device.

In some embodiments, the distribution of mass in the abrasive element 200 may increase the traction that the abrasive element 200 has with material that is deposited on the walls of the vessel lumen. For example, the distribution of mass in the abrasive element 200 may reduce the degree to which the abrasive elements bounces away from the material that it comes into contact with when rotated. Thus, in some embodiments, the distribution of mass of the abrasive element 200 may increase the effectiveness of the atherectomy device. The relative size and shape of the abrasive element 200 may also be varied in order to increase traction. For example, in some embodiments, the abrasive element 200 includes one or more protrusions and/or indentations to increase the traction of the abrasive element with the material to be ablated.

As best shown in FIGS. 2, 4, and 5, the abrasive element 200 may also include a proximal notch 223 in communication with the proximal end of the lumen 203 and a distal notch 221 in communication with the distal end of the lumen 203. Thus, the lumen 203 is open to a top and distally facing direction and is open to a bottom and proximally facing direction. The proximal notch 223 and the distal notch 221 may provide a weld area. That is to say, a weld may be disposed at least partially within the proximal notch 223 and/or the distal notch 221 to secure the abrasive element 200 to the driveshaft 5. In some embodiments, the proximal notch 223 and the distal notch 221 may help to maximize the distance between two offset local centers of mass while maintaining a low profile during delivery of the abrasive element 200. In some embodiments, the notches may remove mass from portions of the proximal and distal ends in order to create the two offset local centers of mass.

In certain embodiments, the abrasive element 200 may move in the axial direction to an angle with respect to the longitudinal axis of the driveshaft 5. In other words, at least a portion of the driveshaft 5 may pass through at least a portion of the distal notch 221 and/or proximal notch 223. Thus, while the abrasive element 200 is coupled to the driveshaft 5 such that the abrasive element 200 is constrained from moving in a longitudinal direction with respect to the driveshaft 5, the abrasive element 200 is not constrained from moving in a transverse and/or lateral longitudinal direction with respect to the driveshaft 5. Accordingly, when the driveshaft 5 and abrasive element 200 are rotated about the longitudinal axis, the proximal and/or distal ends of the abrasive element 200 can move farther away from the central axis of the driveshaft 5. In other embodiments, the abrasive element 200 is attached to the driveshaft 5 so that the abrasive element 200 is constrained from moving relative to the driveshaft 5. In certain embodiments, the abrasive element 200 can be coupled to the driveshaft 5 such that the distal end of the abrasive element 200 cab move relative to the driveshaft in the radial direction.

FIGS. 8A-8D illustrate example positions of the abrasive element 200 attached to a flexible driveshaft 5. As shown in FIGS. 8A-8D, a weld 800 may secure the abrasive element 200 to the driveshaft 5. The weld may be placed at or near the proximal and distal ends of the abrasive element 200. As shown in FIGS. 8B and 8D, the weld 800 may be disposed around the circumference of the lumen 203 and the driveshaft 5.

In FIGS. 8A-8B, the abrasive element 200 attached to a flexible driveshaft 5 is shown in a constrained position within a sheath 801. When the abrasive element 200 is advanced out of the sheath, as shown in FIGS. 8C-8D, the abrasive element 200 can move into an unconstrained position. That is to say, the effective diameter of the abrasive element 200 increases when the abrasive element 200 exits the sheath 801 (e.g., $d_2$ in FIG. 8D is greater in length than $d_1$ in FIG. 8B). In some embodiments, the abrasive element 200 has an unconstrained or deployed profile that is between 10-60% larger, or 35-45% larger, or at least 40% larger than the constrained profile. The portions of the abrasive element 200 that overlap the portions of the driveshaft 5 may be secured together such that the abrasive element 200 and the portion of the driveshaft 5 within the abrasive element 200 move in concert.

FIGS. 8E-8J illustrate example positions of the abrasive element 200 attached to a flexible driveshaft 5 according to another embodiment. FIGS. 8E-8J show the abrasive element 200 attached to a flexible driveshaft 5 with a weld 800. While the attachment means is described as a weld, other attachment means may be used. For example, in some embodiments, an adhesive is used to attach the abrasive element 200 to the flexible driveshaft 5. As shown, the weld 800 is located at the approximate center of the abrasive element 200 and couples an exterior surface of the driveshaft 5 to an interior surface of the lumen 203. However, the weld 800 may cover more or less than the areas shown. For example, in some embodiments, the weld 800 couples the entire length of the lumen 203 to the driveshaft 5. In other embodiments, the weld 800 does not contact all surfaces of a diameter of the lumen 203. As discussed above, the weld 800 prevents the abrasive element 200 from moving in a longitudinal direction with respect to the driveshaft 5. Depending on the type, size, and/or location of the weld 800, the abrasive element 200 may or may not move in a radial direction relative to the driveshaft 5 during rotation.

In certain embodiments, the weld 800 allows for the abrasive element 200 to pivot about the weld 800. That is to say, portions of the abrasive element 200 may move and/or rotate in the radial direction. In other embodiments, the weld 800 is disposed at the proximal and distal ends of the abrasive element as described above. In some embodiments, the portions of the abrasive element 200 that overlap the portions of the driveshaft 5 are secured together such that the abrasive element 200 and the portion of the driveshaft 5 within the abrasive element 200 move in concert.

In FIGS. 8E-8F, the abrasive element 200 attached to a flexible driveshaft 5 is shown in a constrained position within a sheath 801. When the abrasive element 200 is advanced out of the sheath, as shown in FIGS. 8G-8H, the abrasive element 200 can move into an unconstrained position. That is to say, the effective diameter of the abrasive element 200 increases when the abrasive element 200 exits the sheath 801 (e.g., $d_3$ in FIG. 8J is greater in length than $d_2$ in FIG. 8H). In some embodiments, the abrasive element 200 has an unconstrained or deployed profile that is between 10-60% larger, or 35-45% larger, or at least 40% larger than the constrained profile. In certain embodiments, when the abrasive element 200 and flexible driveshaft 5 are rotated, as shown in FIGS. 8I-8J, the centrifugal force will further move the sloped ends 205 of the abrasive element 200 away from the central axis of the flexible driveshaft 5. Thus, the sanding range of the abrasive element 200 may be further increased and the abrasive element 200 can have even larger effective diameter when rotated (e.g., $d_3$ in FIG. 8J is greater in length than $d_2$ in FIG. 8H). Thus, in a tightly closed vessel, the centrifugal forces on the local centers of mass of the distal and proximal ends of the abrasive element 200 can cause the abrasive element 200 to have a larger effective diameter, thus increasing the effectiveness of the device and/or reduce treatment times.

Figure 9:
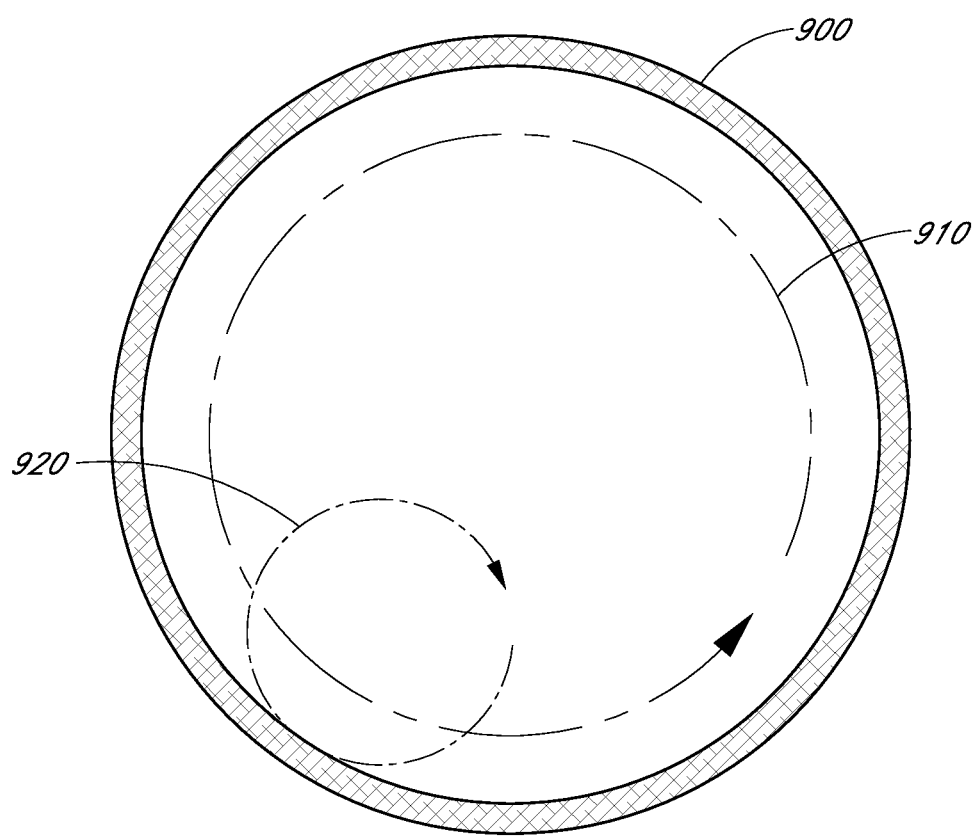
FIG. 9 is a schematic cross-sectional view of a blood vessel and depicts an exemplary motion of the abrasive elements disclosed herein.

FIG. 9 schematically illustrates an example motion of the abrasive elements disclosed herein. As the vessel 900 is opened by the rotating abrasive element 200, 300, 1000, a secondary motion may also be caused and/or enhanced due to the geometry of the abrasive element(s). The small orbit 920 represents the path that the outermost radial facing surfaces of the abrasive element may follow as the driveshaft 5 and abrasive element are rotated. The small orbit 920 may represent the path of the abrasive element 200 as it wobbles with respect to a longitudinal axis passing through the center of the abrasive element. In other words, the effective diameter of the small orbit 920 may be increased by the relative movement of the abrasive element with respect to a longitudinal axis passing through the center of the abrasive element and/or by the physical deformation of the abrasive element. In some embodiments, the small orbit 920 may increase in effective diameter as the abrasive element is rotated. In certain embodiments, for example, the effective diameter of the abrasive element may have a first diameter at a first speed of rotation and an effective second diameter at a second speed of rotation. The second effective diameter may be grater in size than the first effective diameter when the second speed of rotation is greater than the first speed of rotation. In some embodiments, for example, where the abrasive element 200 is attached to the driveshaft 5 so as to allow relative radial movement, this relative radial movement may further increase the size of the small orbit. Thus, the motion of the driveshaft 5 and abrasive element can extend the sweeping area and/or sanding range of the abrasive element beyond the small orbit 920.

In certain embodiments, for example, when the abrasive element has ends with local centers of mass that are distributed opposite from each other and away from the center axis of the driveshaft 5, the rotation of the abrasive element can cause the driveshaft 5 and abrasive element to produce a large orbit 910 due to centrifugal forces (particularly after sufficient space is produced within the lesion and at high rotational speeds, e.g., about 30,000 rpm and above). Thus, the abrasive elements disclosed herein can be configured such that the sweeping area and/or sanding range of the abrasive elements are extended beyond the small orbit 920.

FIGS. 10A-10B illustrate an abrasive element 300 according to a similar embodiment as described above. As shown, the abrasive element 300 has two local centers of mass (having approximated locations at 301 and 303) that are spaced apart and on opposite diagonal corners that are offset from the center of a flexible driveshaft 5. The abrasive element 300 may include a substantially straight lumen extending from the proximal end 313 of the abrasive element 300 to the distal end 311. The abrasive element 300 may be substantially cylindrical in shape. The abrasive element 300 may be attached to the driveshaft 5, as shown in FIG. 10A, such that the distal center of mass 301 is located above the longitudinal center of the driveshaft 5 while the proximal center of mass 303 is located below the longitudinal center of the driveshaft 5. Thus, when the abrasive element 300 is rotated, the sanding range of the abrasive element is increased beyond the small orbit as described above. Furthermore, as shown in FIG. 10B, the abrasive element 300 has a larger effective diameter than the sheath 801 from which it is deployed. The abrasive element 300 may include rounded edges to improve the slidability of the device through a tortuous path and/or through a lumen.

Figure 11:
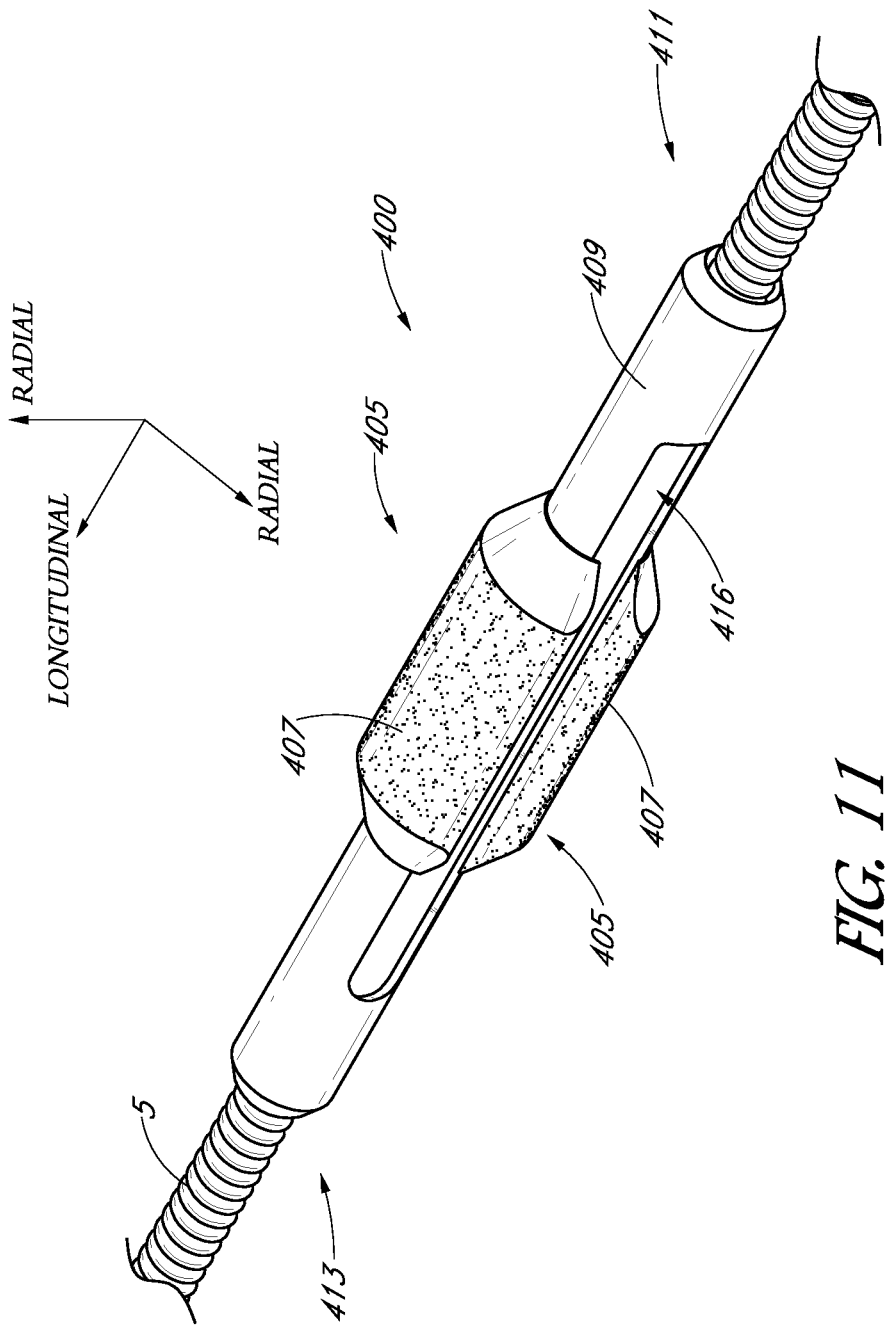
FIG. 11 is a perspective view of an abrasive element according to another embodiment. As shown, the abrasive element includes a slotted tube and two abrasive protrusions disposed on an outer surface of the tube and on opposite sides of the slot.

FIGS. 11-30 illustrate an abrasive element 400 according to another embodiment. As shown for example, in FIG. 11, the abrasive element 400 includes a slotted tube 409 having a least two protrusions extending from the abrasive element 400. As shown, the protrusions comprise a two part bead 405 attached to the abrasive element 400. The abrasive element 400 may have a distal end 411 and a proximal end 413. At least a portion of the bead 405 includes a roughened exterior surface 407. Similar to the embodiments described above, the abrasive element 400 may be coupled to a proximal portion of a flexible driveshaft 5. As will be described in further detail, the slotted tube 409 may be configured to compress such that the abrasive element 400 may pass through a sheath for a low-profile delivery and expand during high speed rotation to increase the sanding range.

Figure 12:
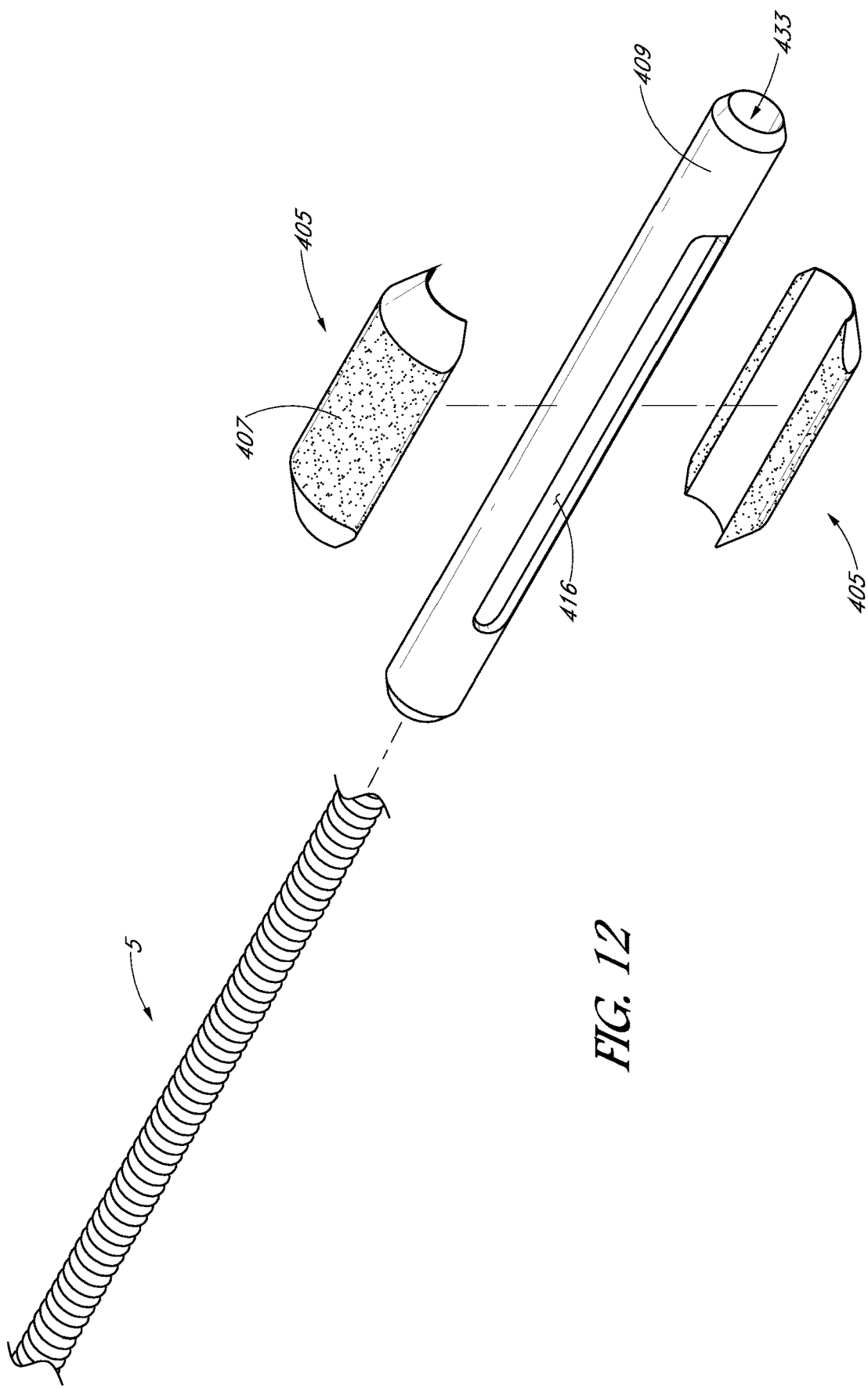
FIG. 12 is an exploded view of the abrasive element of FIG. 11.
Figure 16:
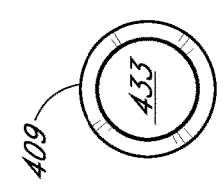
FIG. 16 is a front view of the slotted tube of FIG. 14.
Figure 13:
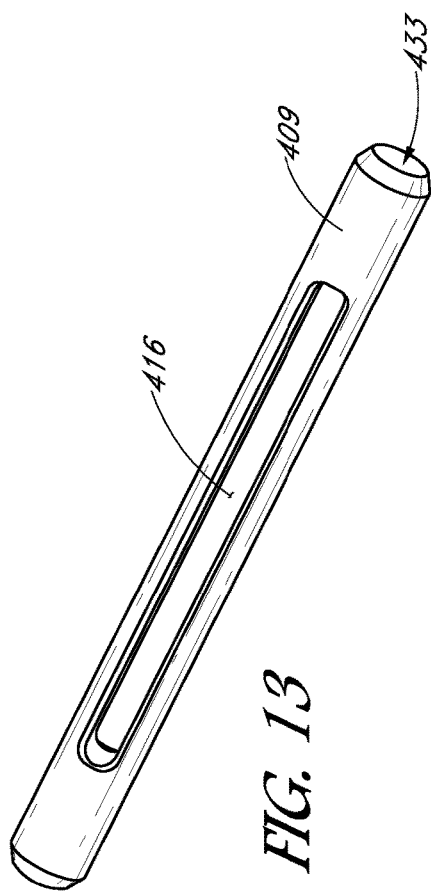
FIG. 13 is a perspective view of the slotted tube of FIG. 12.
Figure 14:
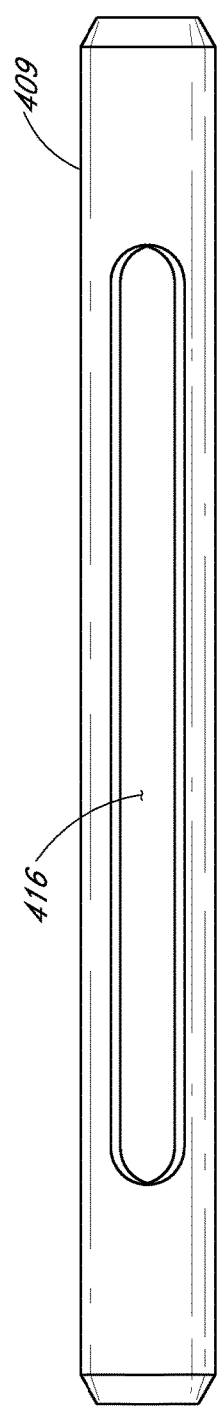
FIG. 14 is a side view of the slotted tube of FIG. 12.
Figure 15:
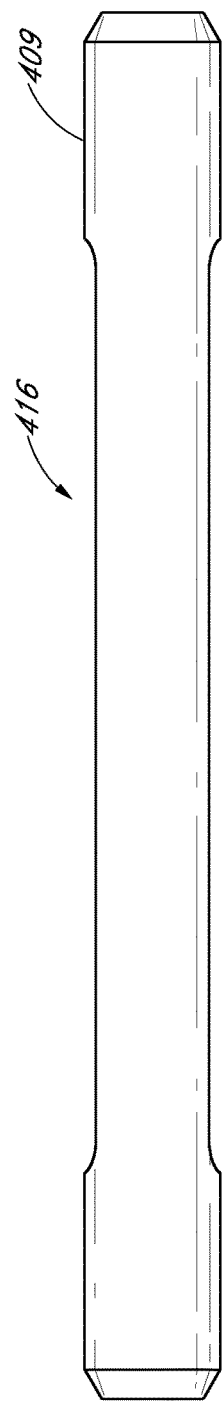
FIG. 15 is a top view of the slotted tube of FIG. 12.
Figure 17:
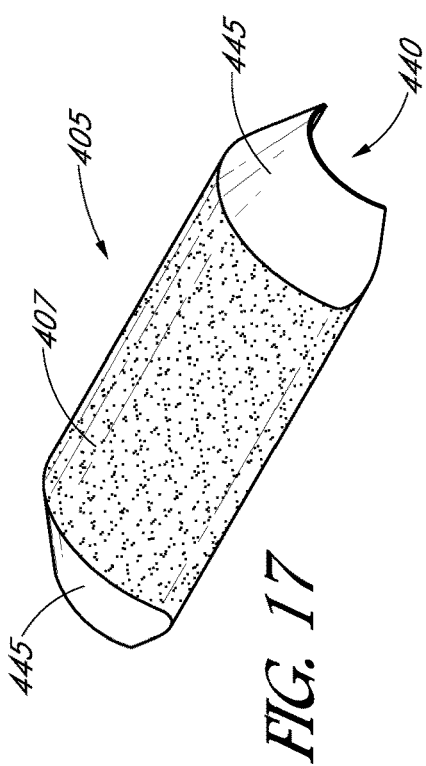
FIG. 17 is a perspective view of one of the abrasive protrusions of FIG. 12.
Figure 19:
FIG. 19 is a bottom view of the abrasive protrusion of FIG. 17.
Figure 18:
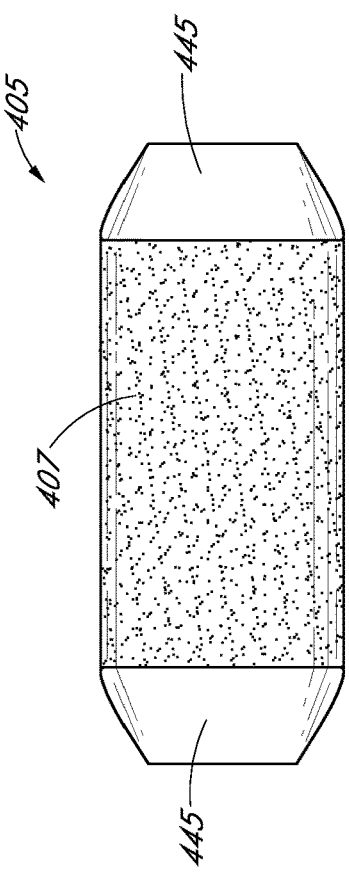
FIG. 18 is a top view of the abrasive protrusion of FIG. 17.
Figure 21:
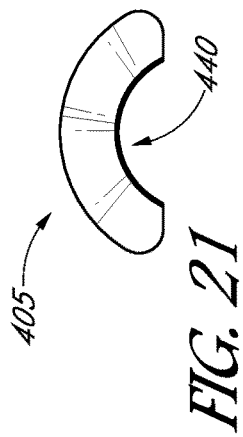
FIG. 21 is a front view of the abrasive protrusion of FIG. 17.
Figure 20:
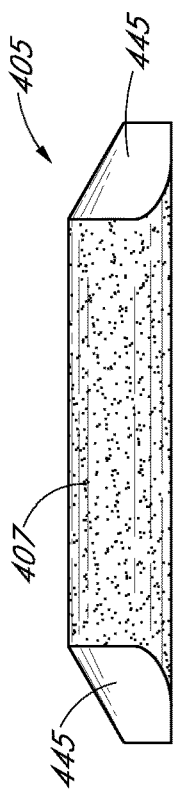
FIG. 20 is a side view of the abrasive protrusion of FIG. 17.

FIG. 12 shows an exploded view of the abrasive element 400. As shown, the two part bead 405 comprises two shaped halves having a roughened outermost surface 407. As shown, the two part bead 405 is shaped such that the surface of the bead 405 facing the slotted tube 409 contacts the curved exterior surface of the slotted tube 409. The two part bead 405 is also shaped such that the bead does not extend over and/or cover any portion of the slot 416. The bead 405 may be coupled to the slotted tube 409 by any suitable means. For example, the bead 405 may be welded, glued, and/or fused to the slotted tube 409. The bead 405 may be made with the same or different materials as the tube 409. In some embodiments, the slotted tube 409 and the beads 405 are made in one piece.

As shown in FIGS. 13-16, the slotted tube 409 may include a substantially cylindrical tube having a lumen 433 extending therethrough in the longitudinal direction. The slot 416 may be generally rectangular in shape and may extend radially through the tube 409 and be in communication with the lumen 433. The tube 409 may be made from one or more materials that are flexible enough to constrict and/or expand under an applied force. In some embodiments, the tube 409 may be configured to constrict in size when an external force is applied and to return to substantially its original form and shape when the external force is removed. In some embodiments, the tube 409 may be configured such that the tube can stretch when an external force is applied and to return to substantially its original form and shape when the external force is removed.

FIGS. 17-21 further illustrate the bead 405. As shown, the bead 405 includes a curved lower surface 440 that is shaped to contact the non-slotted portion of the slotted tube 409. The bead 405 also includes two sloped transitional sections 445 and a central generally cylindrical section that has a roughened surface 407. In some embodiments, the bead 405 is shaped such that it is thicker in areas that are further away from the slot 416 in the slotted tube 409. In some embodiments, the bead 405 is formed of a relatively hard and/or dense material in comparison with the tube 409.

As shown in FIG. 22, when the two part bead 405 is coupled to the slotted tube 409, the mass of each half of the bead 405 is spaced away from the longitudinal center of the flexible driveshaft 5. As such, the abrasive element 400 includes two local centers of mass that are both offset from the longitudinal center of the flexible driveshaft 5. While the local centers of mass of the abrasive element 400 are spaced apart in the radial direction, unlike the embodiments shown in FIGS. 1-10B, the local centers of mass are not spaced apart from one another in the longitudinal direction. However, in some embodiments, the abrasive element 400 may be configured such that the local centers of mass of the abrasive element 400 are offset in both the radial direction and the longitudinal direction. For example, the two bead elements 409 may not be symmetrically attached to the slotted tube 409. In other words, a first bead element may be coupled to the slotted tube 409 such that the proximal-most end of the bead element is positioned over the proximal-most end of the slot 416 while a second bead element may be coupled such that the distal-most end of the bead element is positioned over the distal-most end of the slot 416.

As also shown in FIG. 22, the driveshaft 5 need not pass through the entire length of the abrasive element 400. Thus, the proximal end of the abrasive element 400 may be secured to a distal end of a first driveshaft 5 portion and the distal end of the abrasive element 400 may be secured to a proximal end of a second driveshaft 5 portion. With the driveshaft removed from the center of the abrasive element 400, the abrasive element can be compressed and the two bead elements 409 moved toward each other such that the abrasive element can assume a reduced profile. In other embodiments, the driveshaft 5 passes through the entire length of the abrasive element.

Figure 24:
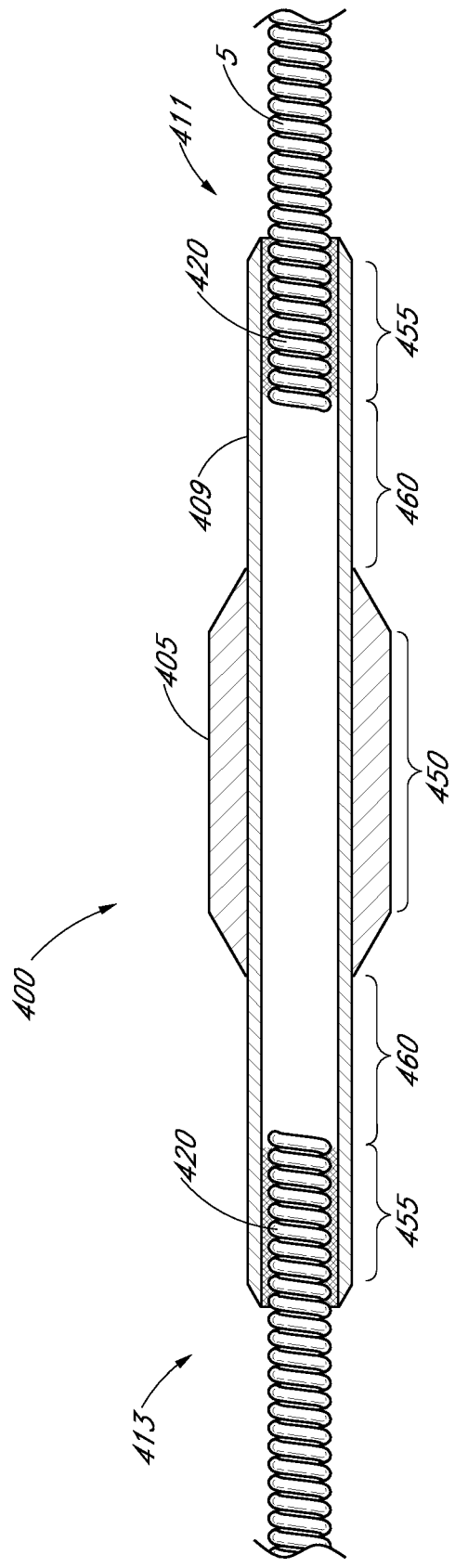
FIG. 24 is a cross-sectional view of the abrasive element of FIG. 11.

FIGS. 22-24 illustrate that the abrasive element 400 may generally include a central abrasive region 450 and proximal and distal attachment regions 455. The central abrasive region 450 may be coupled to the proximal and distal attachment regions 455 with the ligament regions 460. The proximal and distal attachment regions 455 are the portions of the slotted tube 409 that are secured to the flexible driveshaft 5 that extends through the lumen 433 of the slotted tube 409. The proximal and distal attachment regions 455 may include a weld and/or a crimp or any other suitable means of securement. As such, the proximal and distal attachment regions 455 are constrained from moving away from the flexible driveshaft 5. In embodiments where the driveshaft 5 passes through the entire length of the abrasive element, the driveshaft may be secured to the attachment regions 455, but not secured to the ligament regions 460 and the central abrasive region 450. Thus, the ligament regions 460 and the central abrasive region 450 are not constrained and may move towards and/or away from the flexible driveshaft 5.

Figure 25:
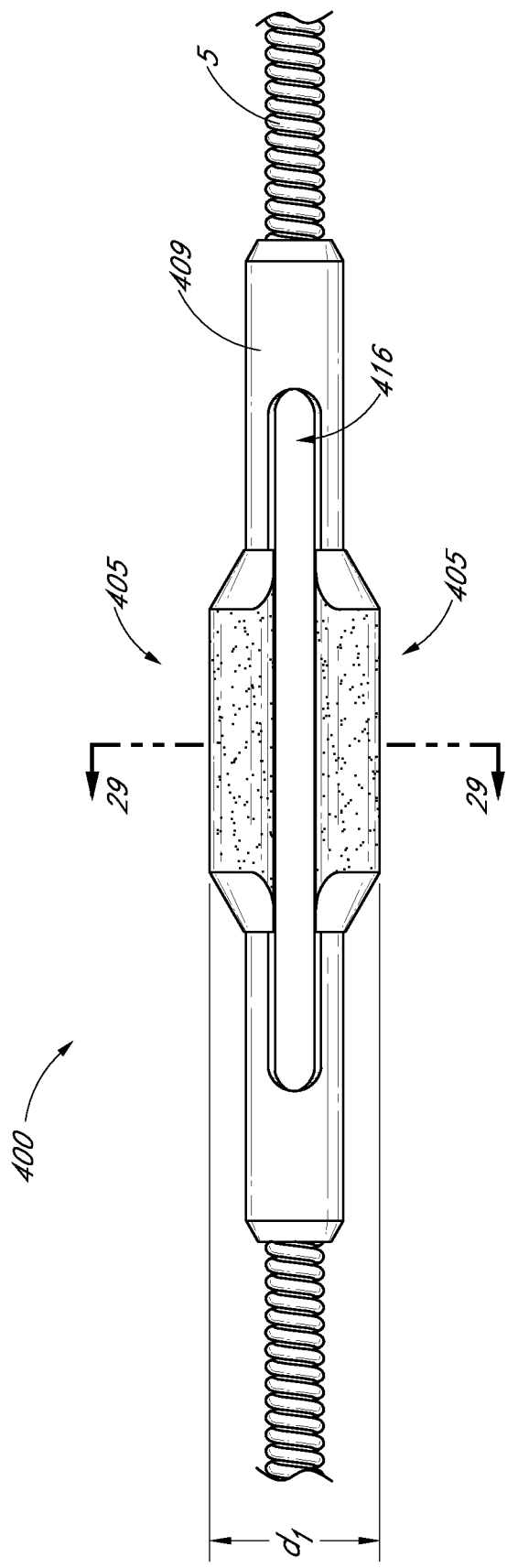
FIG. 25 is the same as FIG. 22 and illustrates the abrasive element in an unconstrained state.
Figure 28:
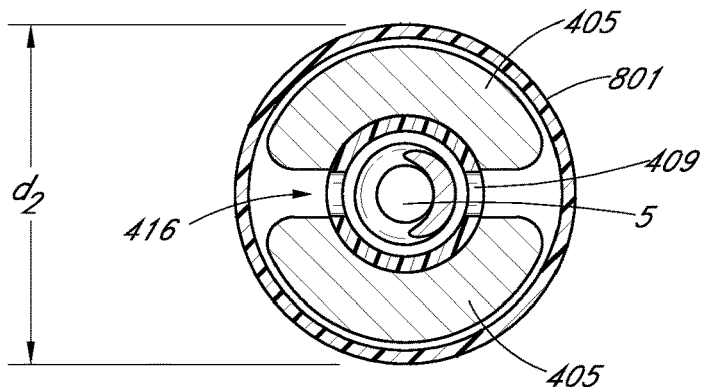
FIG. 28 is a cross-sectional view of FIG. 26 taken about the line 28-28.
Figure 29:
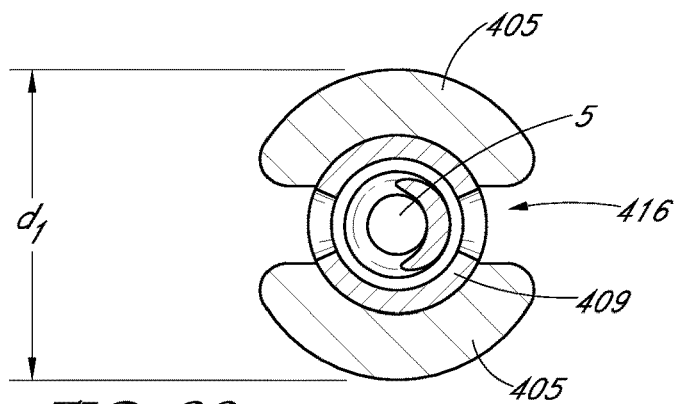
FIG. 29 is a cross-sectional view of FIG. 25 taken about the line 29-29.

FIGS. 25-30 illustrate example positions of the abrasive element 400 attached to a flexible driveshaft 5. The abrasive element 400 is shown in FIGS. 25 and 29 in a resting configuration. The radial thickness of the device in this unconstrained and resting state is labeled as d1. The abrasive element 400 is shown in FIGS. 26 and 28 in a constrained configuration. In FIGS. 26 and 28, the abrasive element 400 is positioned within a sheath 801. In this constrained configuration, the radial thickness of the device is that of the sheath 801 and is labeled as d2. As shown, the radial thickness in the constrained configuration d2 is less than the radial thickness in the unconstrained configuration d1. As shown in FIGS. 26 and 28, in the constrained position, the slotted tube is compressed such that the slot has a width that is less than the width in the unconstrained configuration of FIGS. 25 and 29. In other words, the slotted tube 409 allows for the abrasive element 400 to be compressed in a radial direction. In this way, the abrasive element 400 can have a larger effective diameter than the sheath 801 in which it is delivered in.

In some embodiments, the abrasive element 400 naturally returns to its unconstrained configuration in a relatively short amount of time after it is removed from the sheath 801. In other words, the material of the abrasive element 400 is selected such that the slotted tube 409 springs back to its unconstrained configuration soon after the passive constraint applied by the sheath is removed. In other embodiments, the abrasive element 400 returns to its unconstrained configuration after the abrasive element 400 is rotated at relatively low speeds (e.g. 5,000 rpm or less).

Figure 30:
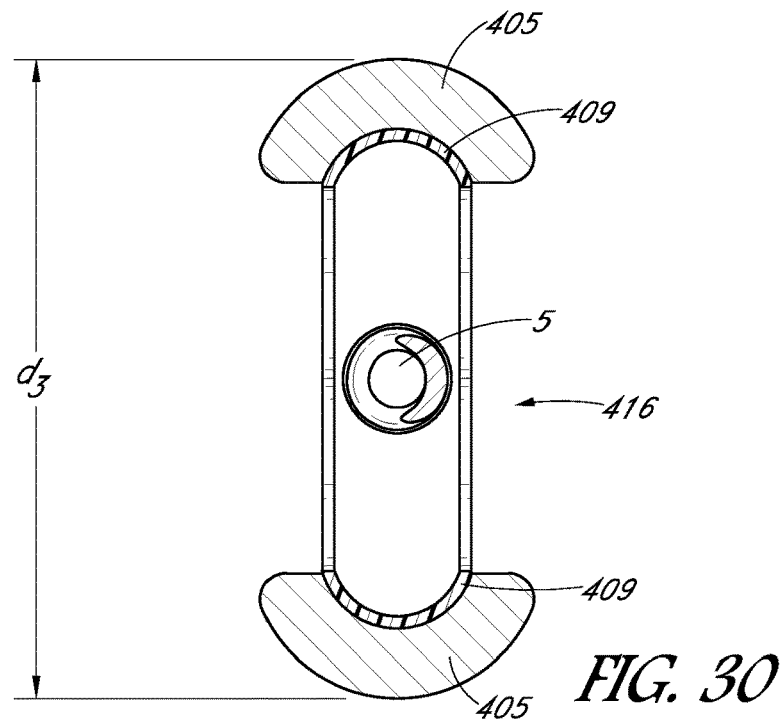
FIG. 30 is a cross-sectional view of FIG. 27 taken about the line 30-30.
Figure 31:
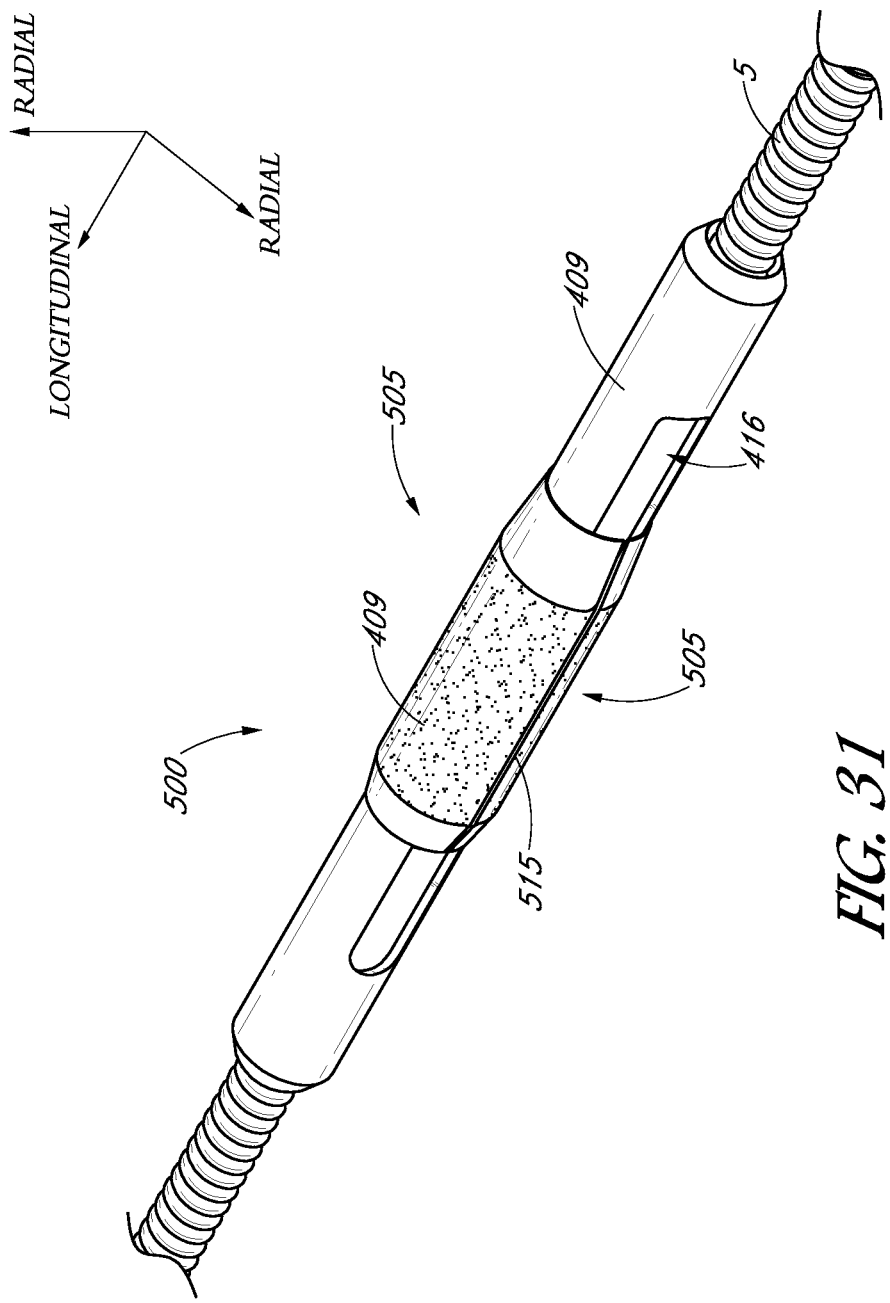
FIG. 31 is a perspective view of an abrasive element according to another embodiment. The embodiment is similar to the embodiment of FIG. 11 except that the two abrasive protrusions at least partially overlap the slot.

In FIGS. 27 and 30, the abrasive element 400 is shown in an expanded configuration. For example, when the abrasive element 400 is rotated at high speeds, centrifugal forces cause the abrasive element 400 to expand as the slotted tube 409 expands. That is to say, the slotted tube 409 expands because the two part bead 405 has local centers of mass that are distributed away from the center axis of the slotted tube 409 and driveshaft 5 and because the rotation causes the bead parts 405 to pull away from the tube axis due to centrifugal force. Thus, when the abrasive element 400 is rotated at high speeds (e.g. about 90,000 rpm and above) the abrasive element 400 may expand to diameter d3, which is greater than d1 and d2. Accordingly, the sanding range of the abrasive element 400 extends beyond its unconstrained diameter d2. While d3 is depicted as substantially larger than d2, it is understood that the diameter of the abrasive element 400 may not increase to such an extent in practice when the device is rotated. The relative sizes of d1-d3 are simply meant to aid the ease of understanding of the device's functionality and are not meant to depict the actual proportions of the expansion in use.

In some embodiments, the abrasive element 400 naturally returns to its unconstrained configuration in a relatively short amount of time after it stops rotating. In other words, the material of the abrasive element 400 is selected such that the slotted tube 409 returns to its unconstrained configuration soon after the driveshaft 5 comes to rest. In other embodiments, the abrasive element 400 returns to near enough to its unconstrained configuration soon after the driveshaft 5 comes to rest and is moved into its constrained configuration when it is withdrawn into the sheath 801.

While the abrasive element 400 has been shown and described as a two piece bead 405 coupled to a slotted tube 409, a unitary construction is also contemplated. Thus, in some embodiments, the slotted tube 409 may have walls in the center area of the slotted tube 409 that are thicker than the walls at the proximal and distal ends of the slotted tubes. At least a portion of the slotted tube may include an abrasive outer surface. In other words, the thickness of the walls on either side of the slot 416 may increase from the two ends of the slotted tube 409 and reach a thickness apex at the center of the slotted tube 409. The change in wall thickness may create two local centers of mass that are distributed away from the center axis of the slotted tube 409 and driveshaft 5. The change in wall thickness may form one or more protrusions extending radially outward from the center of the abrasive element. Thus, when the device is rotated at high speeds, the centrifugal force will cause two local centers of mass to pull the slot open and to radially expand the abrasive element 400. Similarly, materials of differing mass may also be used to create a slotted tube that expands when the slotted tube is rotated at high speeds.

FIGS. 31-36 illustrate an abrasive element 500 according to another embodiment. The abrasive element 500 is similar to abrasive element 400 except that the two part bead 505 is configured to extend at least partially over the slot 416 in the slotted tube 409 when the abrasive element 500 is unconstrained and at rest.

Figure 35A:
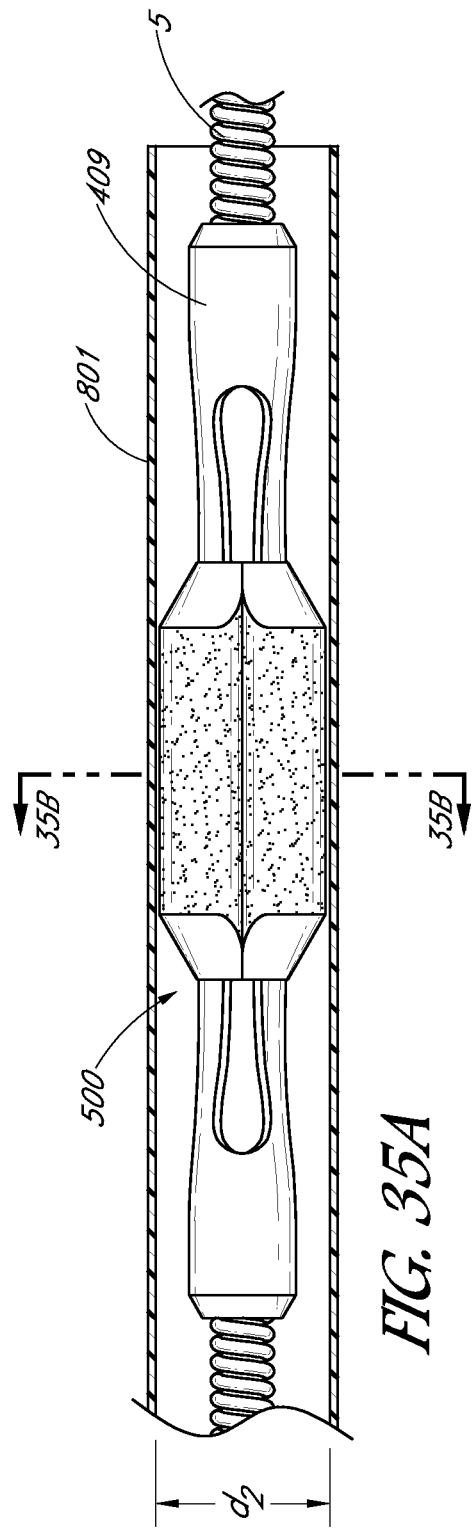
FIG. 35A is a side view of the abrasive element of FIG. 31 positioned within a sheath.
Figure 36A:
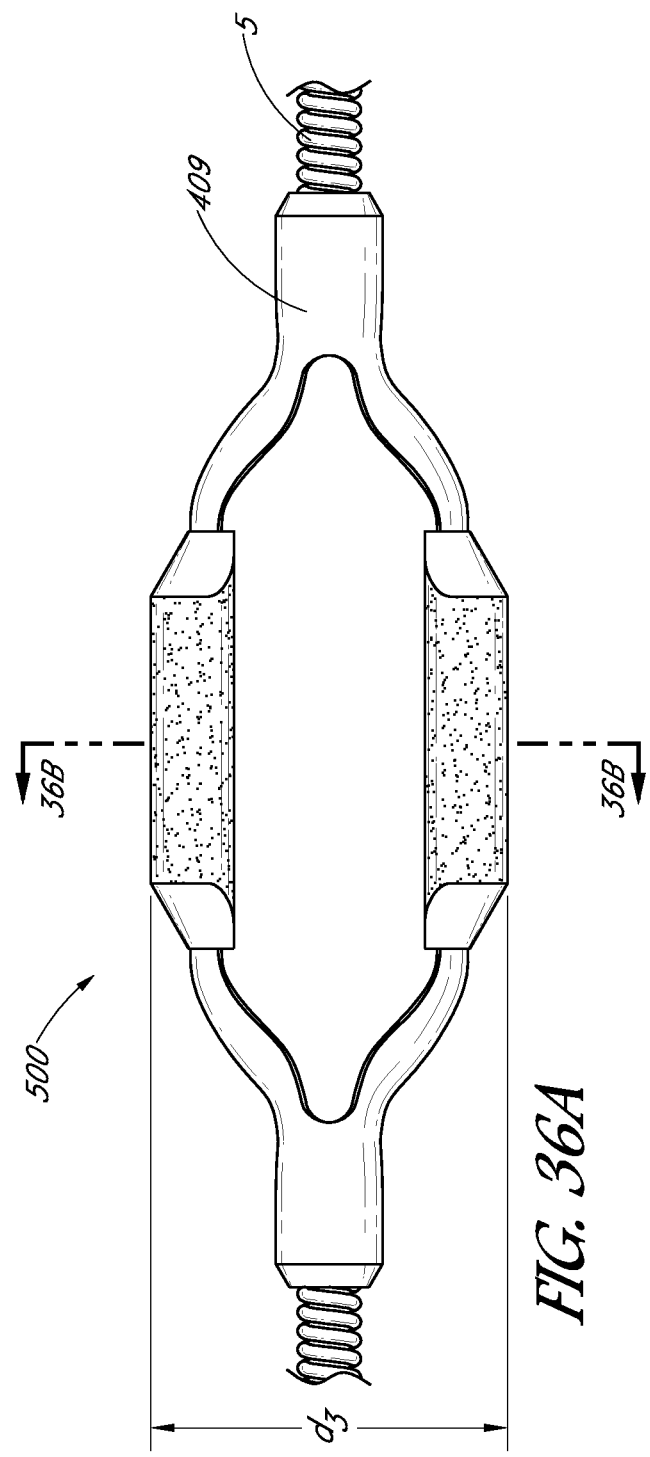
FIG. 36A is a side view of the abrasive element of FIG. 31 when the abrasive element is rotated at high speeds.
Figure 35B:
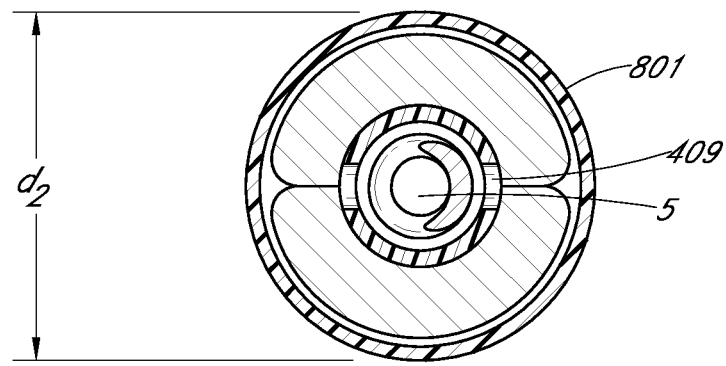
FIG. 35B is a cross-section view of FIG. 35A taken about the line 35B-35B.
Figure 36B:
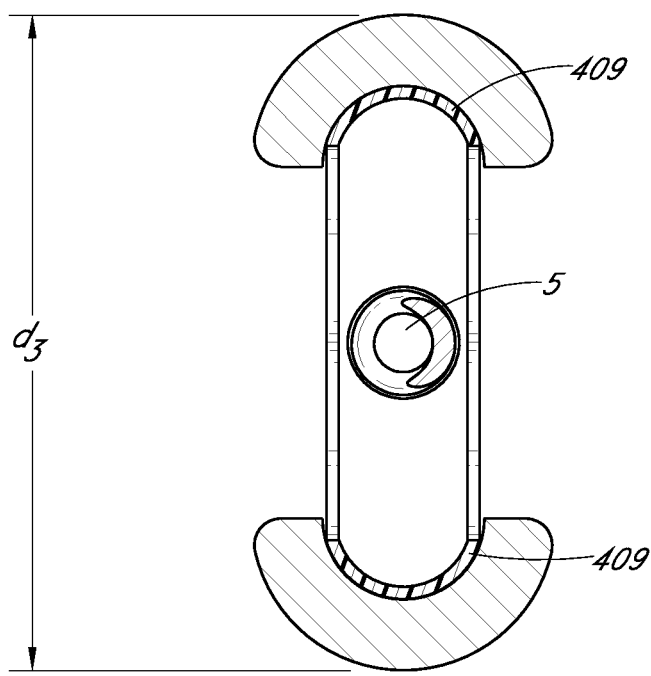
FIG. 36B is a cross-section view of FIG. 36A taken about the line 36B-36B.
Figure 37:
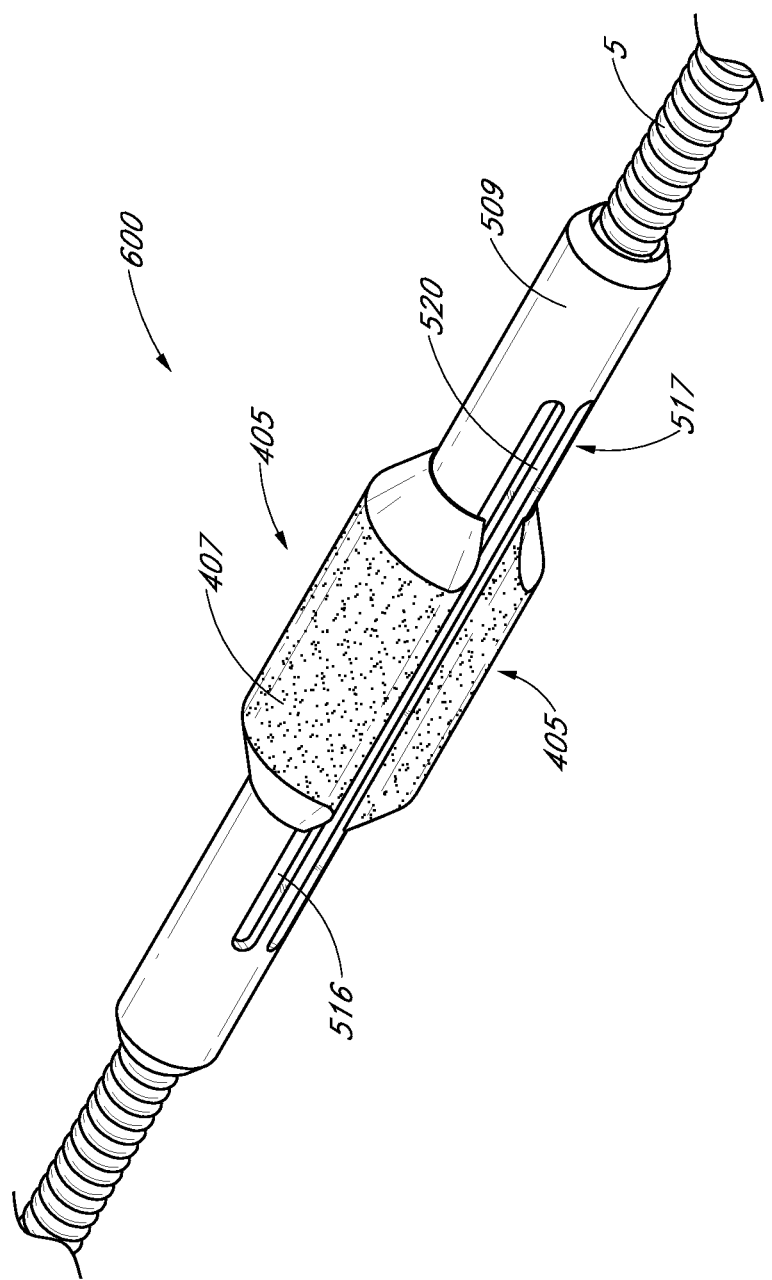
FIG. 37 is a perspective view of an abrasive element according to another embodiment. The embodiment is similar to the embodiment of FIG. 11 except that a bar is positioned over the slot in the slotted tube. This embodiment may be referred to as the double-slotted embodiment. While not shown, a double-slotted version of the device of FIG. 31 is also contemplated.
Figure 38:
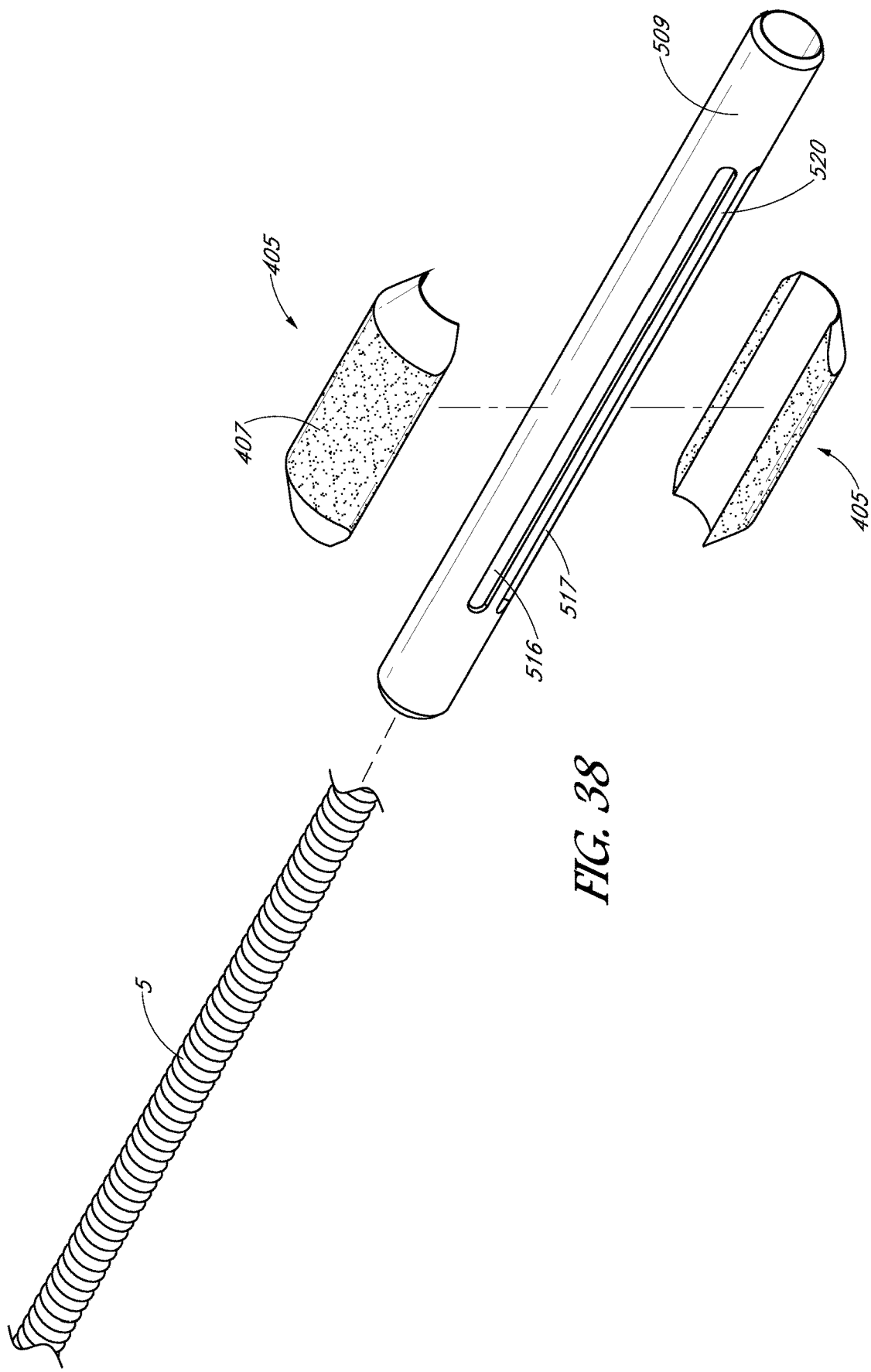
FIG. 38 is an exploded view of the abrasive element of FIG. 37.

As shown, for example, in FIGS. 31-34, the two part bead 505 substantially extends over the slot in the slot 416 in the slotted tube 409 such that only a small gap 515 separates the two part bead 505. When constrained, by a sheath 801 for example, as shown in FIGS. 35A-35B and similar to the embodiment shown in FIG. 26, the two part bead 505 is pressed together. Similar to the embodiment shown in FIGS. 27 and 30, described above, when the abrasive element 500 is rotated at high speeds, as shown in FIGS. 36A-36B, the beads 505 are forced away from one another due to centrifugal force. Thus, the diameter d3 of the abrasive element 500 in motion is greater than the diameter d1 when the device is in its unconstrained configuration.

FIGS. 37-47 illustrate an abrasive element 600 according to another embodiment. As shown, for example in FIGS. 37-40, the abrasive element 600 is similar to abrasive element 400 described above except that the slotted tube 509 includes a support bar 520 extending across the longitudinal length of the slot and on each side of the slotted tube 509 to create two openings 516 and 517. The support bar 520 may help to stiffen the abrasive element 600. As shown in FIG. 42, the slotted tube 509 includes a substantially cylindrical tube having a lumen 433 extending therethrough in the longitudinal direction.

Figure 43:
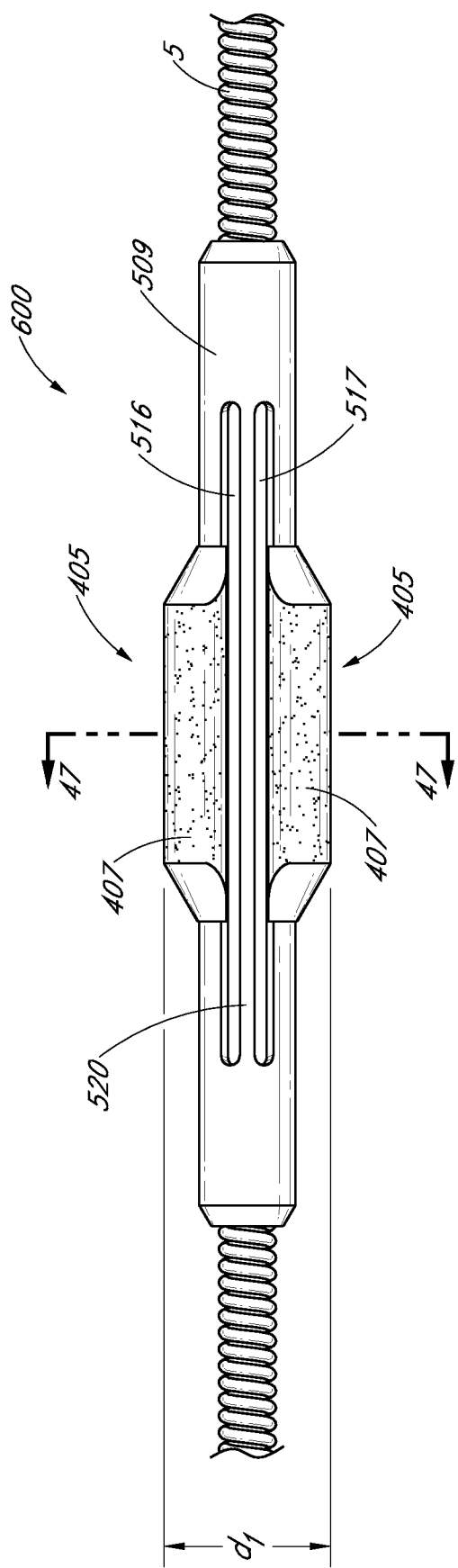
FIG. 43 is a side view of the abrasive element of FIG. 37 and illustrates the abrasive element in an unconstrained state.
Figure 46:
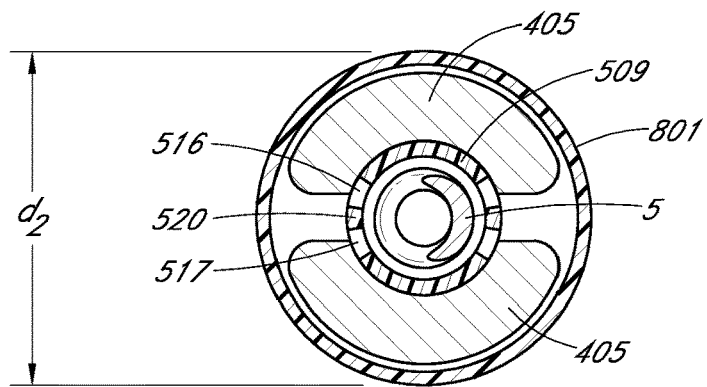
FIG. 46 is a cross-sectional view of FIG. 44 taken about the line 46-46.
Figure 47:
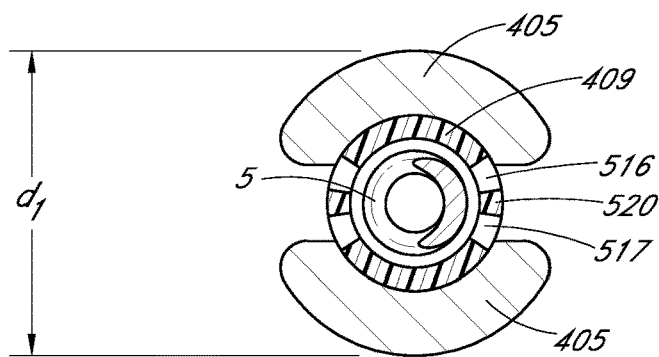
FIG. 47 is a cross-sectional view of FIG. 43 taken about the line 47-47.
Figure 48:
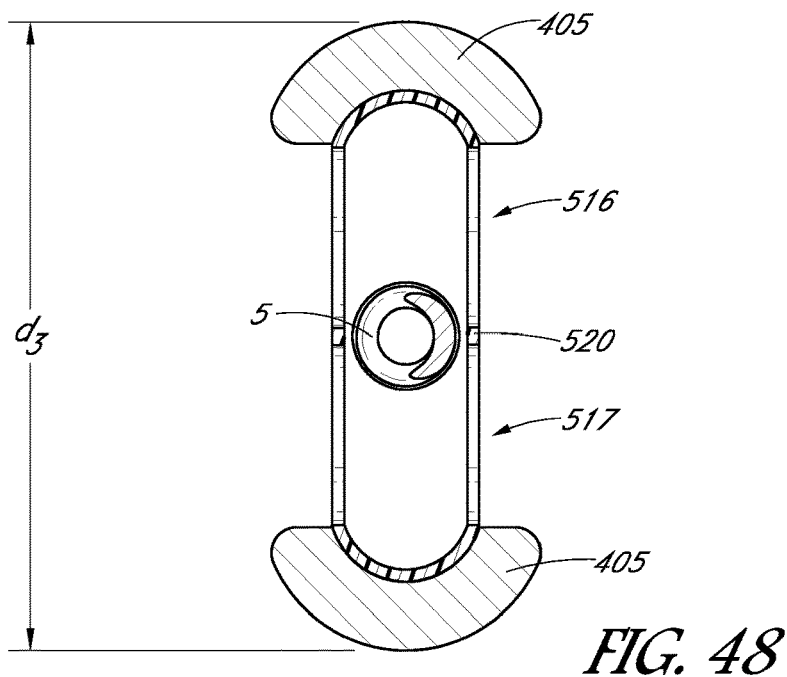
FIG. 48 is a cross-sectional view of FIG. 45 taken about the line 48-48.
Figure 49:
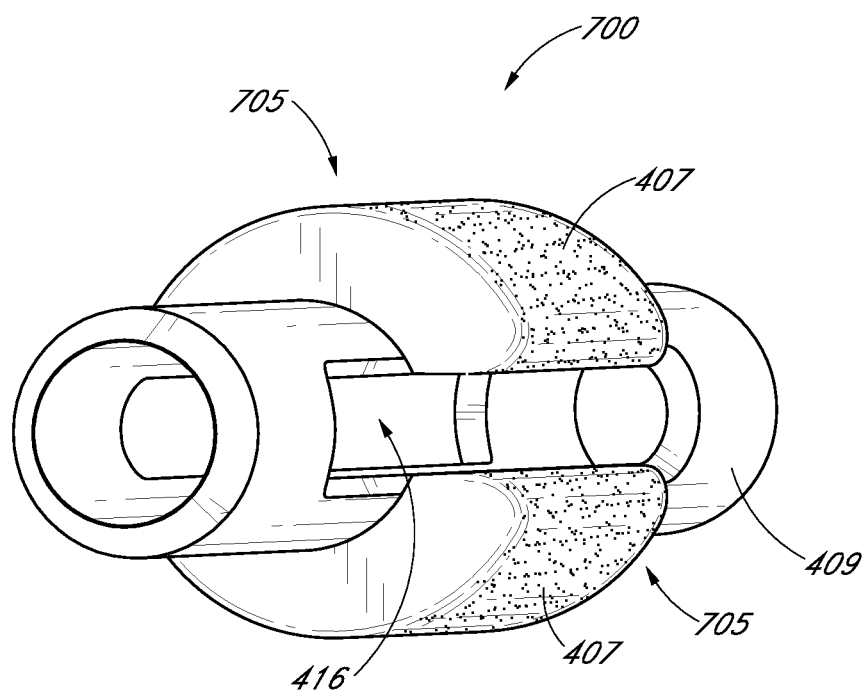
FIG. 49 is a perspective view of an abrasive element according to another embodiment. The embodiment of FIG. 49 is similar to that of FIG. 11 but includes differently shaped abrasive protrusions than FIG. 11.
Figure 53:
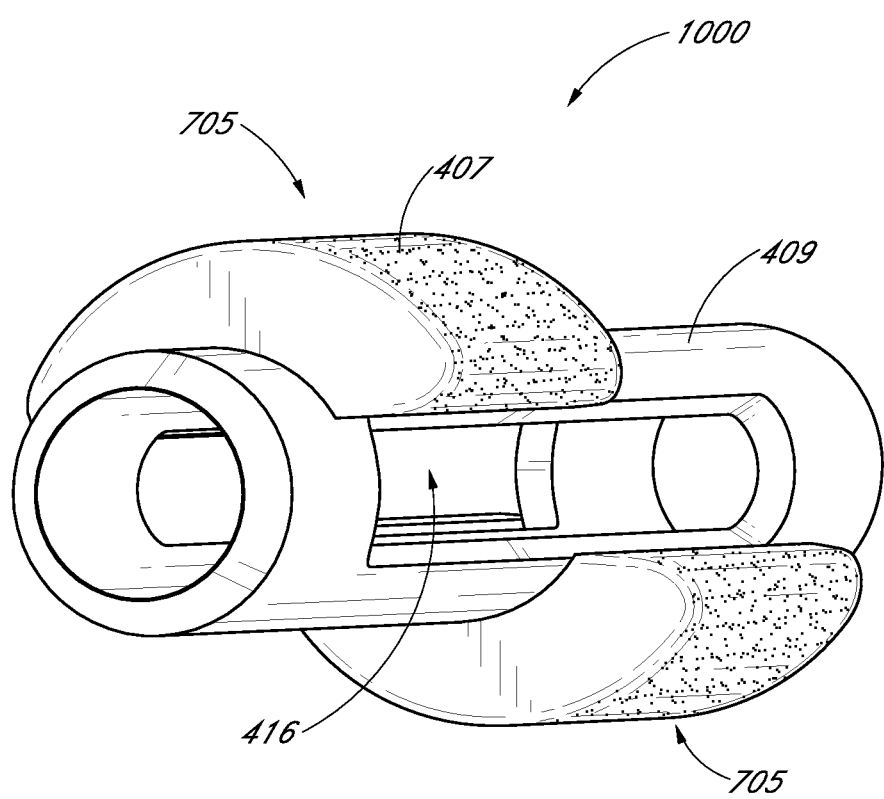
FIG. 53 is a perspective view of an abrasive element according to a different embodiment. The embodiment of FIG. 53 is similar to that of FIG. 49 except that the abrasive protrusions are offset from one another along a longitudinal axis.
Figure 54:
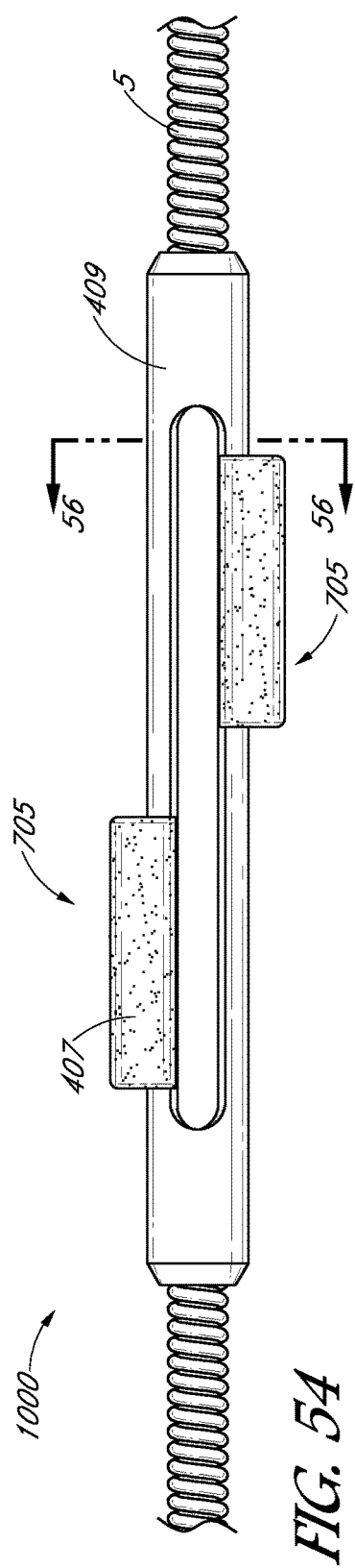
FIG. 54 is a side view of the abrasive element of FIG. 53.
Figure 55:
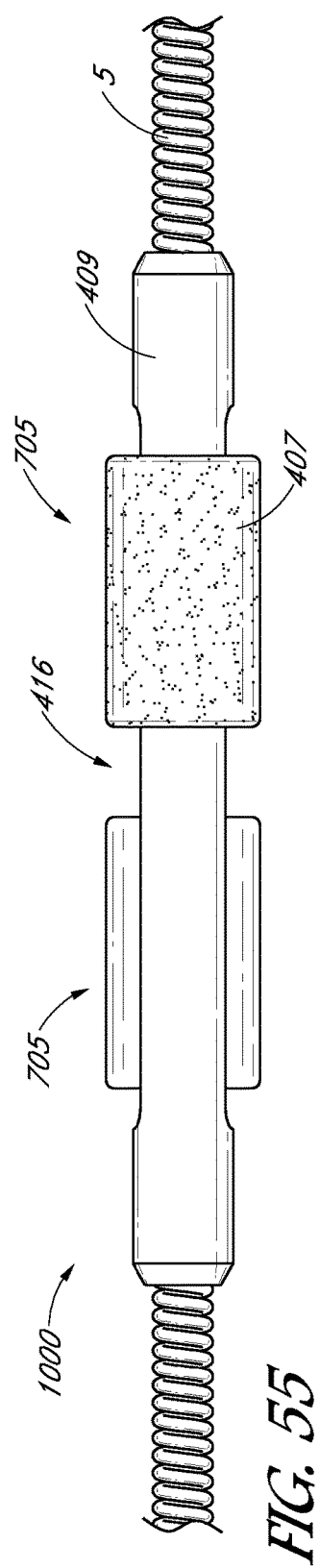
FIG. 55 is a top view of the abrasive element of FIG. 54.
Figure 56:
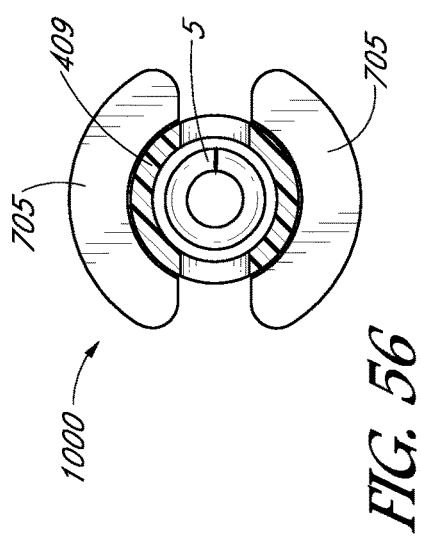
FIG. 56 is an axial view of the abrasive element of FIG. 54.

FIGS. 43-48 illustrate various configurations of the abrasive element 600 in use. Similar to FIGS. 26 and 35A, the abrasive element 600 may be constrained to a smaller maximum diameter when an external force is applied to, for example, the two part bead 405. As shown in FIG. 44, the slotted tube 509 may be compressed within a sheath 801 such that the radial width of the slotted tube 509 is reduced. As described above, the abrasive element 600 may return to its unconstrained configuration when it is removed from the sheath 801 as shown in FIG. 43. Similar to the embodiments shown in FIGS. 27, 30, and 36A, and described above, the abrasive element 600 may expand in diameter when the abrasive element 600 is rotated at high speeds and may return to the unconstrained configuration when the rotation is stopped.

FIGS. 49-52 illustrate an abrasive element 700 according to another embodiment that is similar to the abrasive element 400 (as shown for example in FIG. 11) except that the two part bead 705 is differently shaped. While the two-part bead 705 is depicted as not extending over the slot 416 in the slotted tube 409, in some embodiments the two-part bead 705 does extend at least partially or completely over the slot.

FIGS. 53-56 illustrate an abrasive element 1000 according to another embodiment that is similar to the abrasive element 700 except that the beads 705 are offset from one another in the longitudinal direction. Thus, as described above, the sanding range of the abrasive element 1000 extends beyond the small orbit when the abrasive element 1000 is rotated by the driveshaft 5.

The atherectomy systems disclosed herein may be used, for example, in the following manner. A guidewire may be inserted into a patient and advance over an area of interest. A rotatable driveshaft having an abrasive element attached to a proximal portion of the driveshaft may be advanced over the guidewire. The rotatable driveshaft and abrasive element may be advanced through a sheath. In some embodiments, the abrasive element expands in a radial direction when it is advanced out of the sheath. In some embodiments, the abrasive element expands to a first diameter when it is rotated at a first speed and expands to a second diameter that is greater than the first diameter when the abrasive element is rotated at a second speed that is greater than the first speed. The abrasive element may be advanced over an arterial lesion. The abrasive element may be rotated to ablate the arterial lesion. Fluid may or may not be delivered through the sheath. The arterial lesion may be ablated and the abrasive element, driveshaft, sheath, and guidewire may be removed from the patient. In some embodiments, suction is applied and material is withdrawn through the driveshaft.

Those of skill in the art will recognize that the disclosed aspects and features shown herein are not limited to any particular embodiment of an atherectomy system, and atherectomy systems that include one or more of the features herein described can be designed for use with a variety of medical procedures. Moreover, the skilled artisan will recognize the interchangeability of various features from different embodiments. For example, the features of the abrasive elements disclosed in the various embodiments can be switched between embodiments. In addition to the variations described herein, other known equivalents for each feature can be mixed and matched by one of ordinary skill in this art to construct abrasive elements and atherectomy techniques in accordance with principles of the present invention.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A method of ablating a lesion in a vessel, comprising:
advancing a guidewire through the vessel;
advancing a sheath over the guidewire, the sheath having a proximal end, a distal end, and a lumen extending therethrough;
advancing a flexible driveshaft over the guidewire and through the sheath, the driveshaft having a first driveshaft portion having a first driveshaft portion distal end, a second driveshaft portion having a second driveshaft portion proximal end, a slotted tube having a slotted tube proximal end and a slotted tube distal end, wherein the slotted tube proximal end is mounted to the first driveshaft portion distal end, the slotted tube distal end is mounted to the second driveshaft portion proximal end and the slotted tube spacing the first driveshaft portion and the second driveshaft portion apart from one another to provide a gap between the first driveshaft portion and the second drive shaft portion, and an abrasive element attached to and protruding from an outer surface of the slotted tube, wherein the slotted tube is collapsible into the gap in a constrained state when the slotted tube and abrasive element are advanced through the sheath such that at least a portion of the slotted tube has a diameter smaller than a diameter of the driveshaft in the constrained state;
advancing the abrasive element out of the distal end of the sheath;
radially expanding a diameter of the slotted tube such that the slotted tube expands away from the gap in an expanded state when the slotted tube and abrasive element are rotated by the driveshaft; and
ablating the lesion.

2. The method of claim 1, wherein the abrasive element has a first diameter and the abrasive element is constrained to a second diameter that is less than the first diameter when the abrasive element is advanced through the sheath.

3. The method of claim 1, wherein the abrasive element comprises at least two portions protruding from the outer surface of the body and on opposite sides of the slotted tube.

4. The method of claim 3, wherein the at least two portions are disposed at different longitudinal locations along the body.

5. The method of claim 1, wherein each of the first drive shaft portion and the second drive shaft portion comprise a flexible coil and the gap is provided by a discontinuity in the coil.

6. A method of making an atherectomy device, comprising:
providing a flexible, elongated, rotatable driveshaft that is sized and shaped for insertion into a lumen, the drive shaft having a first driveshaft portion having a first driveshaft portion distal end, a second driveshaft portion having a second driveshaft portion proximal end;
providing a body having a distal end, a proximal end, and a radially expandable, substantially cylindrical structure at a location between the distal end and the proximal end,
coupling the distal end of the body to the second driveshaft portion proximal end and the proximal end of the body to the first driveshaft portion distal end thereby spacing the first driveshaft portion from the second driveshaft portion to provide a gap between the first driveshaft portion and the second drive shaft portion; and
disposing at least two abrasive elements on the body and distributing the at least two abrasive elements around the radially expandable, substantially cylindrical structure, wherein the body is collapsible into the gap in a constrained state such that at least a portion of the body has a diameter smaller than a diameter of the driveshaft when the body and abrasive element are advanced through the sheath and the body is expandable away from the gap in an expanded state when the body and abrasive element are rotated by the driveshaft.

7. The method of claim 6, wherein the radially expandable, substantially cylindrical structure comprises a generally rectangular slot extending through a side of the body.

8. The method of claim 7, wherein the at least two abrasive elements are disposed so that rotating the driveshaft pushes the at least two abrasive elements away from each other and increases a width of the slot when the substantially cylindrical structure is in the expanded state.

9. The method of claim 7, wherein a bar extends from a proximal end of the slot to a distal end of the slot.

10. The method of claim 6, wherein the body comprises an elongated tube.

11. The method of claim 6, wherein the body comprises nitinol.

12. The method of claim 6, wherein the radially expandable, substantially cylindrical structure of the body has a slot extending through a side of the body, wherein the slot is compressed such that a compressed width of the slot in the constrained state is less than an unconstrained width of the slot in a resting configuration of the radially expandable, substantially cylindrical structure, wherein the unconstrained width of the slot in the resting configuration is less than a radially expanded width of the slot in the expanded state of the radially expandable, substantially cylindrical structure.

13. The method of claim 6, wherein at least one of the abrasive elements comprise tungsten.

14. The method of claim 6, wherein each of the abrasive elements comprises a material that is different from a material that the body comprises.

15. The method of claim 6, wherein the at least two abrasive elements are solid.

16. A method of making an atherectomy device, comprising:
- providing a flexible, elongated, rotatable driveshaft, advanceable through a lumen; and
- disposing a generally cylindrical abrasive element on the driveshaft, wherein the generally cylindrical abrasive element has a first end portion with a first radial offset center of mass, the first radial offset center of mass is offset in a first radial direction and the generally cylindrical abrasive element has a second end portion with a second radial offset center of mass proximal to and opposite of the first radial offset center of mass and is offset in a second radial direction, and the second radial direction is predominantly opposite of the first radial direction.

17. The method of claim 16, wherein the generally cylindrical abrasive element comprises a waist disposed between the first end portion and the second end portion.

18. The method of claim 16, wherein the generally cylindrical abrasive element has an eccentric shape.

19. The method of claim 16, wherein the generally cylindrical abrasive element includes an exterior surface that is rough compared to the exterior surfaces of the driveshaft.

20. The method of claim 16, wherein the first end portion and the second end portion of the generally cylindrical abrasive element have a higher density than the remainder of the generally cylindrical abrasive element.

* * * * *